(12) United States Patent
Oku et al.

(10) Patent No.: US 10,583,184 B2
(45) Date of Patent: Mar. 10, 2020

(54) ARTIFICIAL ANTIGEN PRODUCED USING PARTIAL SEQUENCE OF ENOLASE PROTEIN ORIGINATED FROM PLASMODIUM FALCIPARUM, AND METHOD FOR PRODUCING SAME

(71) Applicant: Shigeyuki Kano, Tokyo (JP)

(72) Inventors: Hiroyuki Oku, Maebashi (JP);
Shigeyuki Kano, Tokyo (JP);
Kazuhiko Yano, Tokyo (JP)

(73) Assignee: Shigeyuki Kano, Tokyo (JP)

( * ) Notice: Subject to any disclaimer, the term of this patent is extended or adjusted under 35 U.S.C. 154(b) by 0 days.

(21) Appl. No.: 15/531,122

(22) PCT Filed: Nov. 27, 2015

(86) PCT No.: PCT/JP2015/083437
§ 371 (c)(1),
(2) Date: May 26, 2017

(87) PCT Pub. No.: WO2016/084944
PCT Pub. Date: Jun. 2, 2016

(65) Prior Publication Data
US 2017/0312353 A1 Nov. 2, 2017

(30) Foreign Application Priority Data
Nov. 28, 2014 (JP) ................................. 2014-241420

(51) Int. Cl.
| | |
|---|---|
| *A61K 39/00* | (2006.01) |
| *A61K 39/02* | (2006.01) |
| *A61K 39/015* | (2006.01) |
| *C12N 9/88* | (2006.01) |
| *G01N 33/53* | (2006.01) |
| *A61K 38/00* | (2006.01) |
| *C07K 14/445* | (2006.01) |
| *A61K 47/64* | (2017.01) |
| *A61K 9/16* | (2006.01) |
| *G01N 33/543* | (2006.01) |
| *G01N 33/569* | (2006.01) |
| *G01N 33/68* | (2006.01) |

(52) U.S. Cl.
CPC .......... *A61K 39/015* (2013.01); *A61K 9/1647* (2013.01); *A61K 9/1658* (2013.01); *A61K 9/1682* (2013.01); *A61K 38/00* (2013.01); *A61K 47/646* (2017.08); *C07K 14/445* (2013.01); *C12N 9/88* (2013.01); *C12Y 402/01011* (2013.01); *G01N 33/53* (2013.01); *G01N 33/543* (2013.01); *G01N 33/56905* (2013.01); *G01N 33/6854* (2013.01); *A61K 2039/575* (2013.01); *A61K 2039/6068* (2013.01); *G01N 2333/445* (2013.01); *G01N 2333/988* (2013.01); *G01N 2800/52* (2013.01)

(58) Field of Classification Search
CPC .............................. A61K 39/00; A61K 39/015
USPC .......... 424/184.1, 185.1, 234.1, 265.1, 268.1
See application file for complete search history.

(56) References Cited

U.S. PATENT DOCUMENTS

2007/0269377 A1 11/2007 Oku et al.
2015/0285796 A1 10/2015 Oku et al.

FOREIGN PATENT DOCUMENTS

| EP | 0 450 715 A1 | 10/1991 |
|---|---|---|
| JP | H08-231423 A | 9/1996 |
| JP | 2002-371098 A | * 12/2002 |
| JP | 2002-371098 A | 12/2002 |
| JP | 2009-256324 A | 11/2009 |
| JP | 2012-240940 A | 12/2012 |
| WO | WO 2006/035815 A1 | 4/2006 |
| WO | WO 2014/073464 A1 | 5/2014 |

OTHER PUBLICATIONS

Dictionary of Mictrobiology and Molecular Biology, 2nd ed., eds. Singleton and Sainsbury, 1993, John Wilely & Sons, NewYork, NY. p. 452.*
Noi et al., "Solution-Phase Synthesis and Structural Analysis of Multiple Antigenic Peptides Having Partial Sequences of *Plasmodium Falciparum* Enolase," *Peptide Science*, 2002: 309-312 (2003).

(Continued)

*Primary Examiner* — Rodney P Swartz
(74) *Attorney, Agent, or Firm* — Leydig, Voit & Mayer, Ltd.

(57) ABSTRACT

The invention provides a bioactive peptide including a partial amino acid sequence of *Plasmodium falciparum* enolase, and having a molecular structure compatible with a specification setting for a GMP-compliant production process. The peptide has a structure in which two peptides, each having an amino acid sequence of A01-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-A02 (SEQ ID NO: 1) or A03-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Lys-Ser-Leu-Val-Lys-Thr-A04 (SEQ ID NO: 2) are linked by amide bonds between the respective carboxy termini of the two peptides and two amino groups of Lys in a linker peptide represented by Lys-A05-Cys-A06 and arranged in the form of a two-forked branch, wherein each of A01 to A06 represents an amino acid residue in a number of an arbitrary number including 0. The peptide preferably has a dimerized structure in which two of the above described peptides are linked by an S—S bond between the Cys residues in the linker peptide sequences included in the respective two peptides.

11 Claims, 14 Drawing Sheets
Specification includes a Sequence Listing.

(56) References Cited

OTHER PUBLICATIONS

Kokubo et al., "Synthesis of Multiple-Antigenic Peptides Having Partial Sequence of Enolase," *Peptide Science*, 2001: 331-334 (2002).
Japanese Patent Office, International Preliminary Report on Patentability in International Patent Application No. PCT/JP2015/083437 (dated Jun. 8, 2017).
Kobuko et al., "Synthesis of Multiple-Antigenic Peptides Having Partial Sequence of Enolase," *Peptide Science*, 2001: 331-334 (2002).
Japanese Patent Office, International Search Report in International Patent Application No. PCT/JP2015/083437 (dated Feb. 16, 2016).
European Patent Office, Extended European Search Report in European Patent Application No. 15862466.8 (dated May 30, 2018).

* cited by examiner

FIG. 10

Human alpha enolase (SEQ ID NO: 4)
P. falciparum enolase (SEQ ID NO: 3)
(The underline indicates the enolase partial sequence AD22)

```
  1   MSILKIH---AREIFDSRGNPTVEVDLFTSKGLFRAAVPSGASTGIYEALELRDNDKTR   56
  1   MAHVITRINAREILDSRGDPTVEVDLETNLGLFRAAVPSGASTGIYEALELRDNDKSR    58

57   YMGKGVSKAVEHINKTIAPALVSKKLNVTEQEKIDKLMIE-MDGTEN------KSKFGA  109
 59   YLGKGVQKAIKNINELIAPKLI---GMNCTEQKKIDNLMVEELDGSKNEWGWSKSKLGA  114

110   NAILGVSLAVCKAGAVEKGVPLYRHIADLAGN-SE-VILPVPAFNVINGGSHAGNKLA   165
115   ANILAISMAVCRAGAAPNKVSLYKYLAQLAGKKSDQMVLPVPCLNVINGGSHAGNKKS   172

166   MQEFMILPVGAANFREAMRIGAEVYHNLKNVIKEKYGKDATNVGDEGGFAPNILENKE   223
173   YEQYMIVPVGAPSYKEALRYGAEVTHTLKSEIKKKYGIDATNVGDEGGFAPNILNANE  230

224   GLELLKTAIGKAGYTDKVVIGMDVAASEFFRSG-K-YDLDFKSPD-DPSRYISPDQLA   279
231   ALDLLVTAIKSAGYEGKVKIAMDVAASEFYNSENKTYDLDFKTPNNDKSLVKTGAQLV   288
                                       AD22              AT28
280   DLYKSFIKDYPVVSIEDPFDQDDWGAWQKFTASAGI--QVVGDDLTVTNPKRIAKAVN  335
289   DIYIDLVKKYPIVSIEDPFDQDDWENYAKLTAAIGKDVQIVGDDLLVTNPTRITLALE  346

336   EKSCNCLLLKVNQIGSVTESLQACKLAQANGWGVMVSHRSGETEDTFIADLVVGLCTG  393
347   KNACNALLLKVNQIGSITGAIEACLLSQKNNWGVMVSHRSGETEDVFIADLVVALRTG  404

394   QIKTGAPCRSERLAKYNQLLRIEEELGSKAKFAGRNFRNPLAK  436
405   QIKTGAPCRSERNAKYNQLLRIEESLGNNAVFAGEKFRLQLN   446
```

FIG. 14

Comparing the homology of binding sequences

| Findings of the present inventors | | |
|---|---|---|
| *Plasmodium falciparum* (peptide 8, strongly bound) (SEQ ID NO: 17) | VAASEFYNSE | NKT YDLDFKTPNNDKSLVKTGAQLVK |
| *Plasmodium falciparum* (peptide 3, strongly bound) (SEQ ID NO: 12) | | NKT YDLDFKT K |
| Hitherto reported sequences | | |
| *Plasmodium falciparum* (peptide, inhibited) (SEQ ID NO: 18) (Proc Natl Acad Sci USA. 2011, vol. 108, pp. 17153-17158.) | | <u>KSLVK</u> |
| *Streptococcus pneumoniae* (peptide, inhibited) (SEQ ID NO: 19) (Mol Microbiol. 2003, vol. 49, pp. 411-423.) | CASSEF-------- | --<u>Y</u>DKERKV<u>Y</u>DYT<u>K</u>FEGEGAAVRT |
| Human (phage display, bound) (SEQ ID NO: 20) (Thromb Haemost. 1997, vol. 78, pp. 1097-103.) | VAASEFFRSG | -K-<u>YDLDFKSPD-DPSRYISPDQLA</u> |

SEQUENCE LISTING

<160> NUMBER OF SEQ ID NOS: 21

<210> SEQ ID NO 1
<211> LENGTH: 22
<212> TYPE: PRT
<213> ORGANISM: Plasmodium falciparum

<400> SEQUENCE: 1

Ala Ser Glu Phe Tyr Asn Ser Glu Asn Lys Thr Tyr Asp Leu Asp Phe
1               5                   10                  15

Lys Thr Pro Asn Asn Asp
            20

<210> SEQ ID NO 2
<211> LENGTH: 28
<212> TYPE: PRT
<213> ORGANISM: Plasmodium falciparum

<400> SEQUENCE: 2

Ala Ser Glu Phe Tyr Asn Ser Glu Asn Lys Thr Tyr Asp Leu Asp Phe
1               5                   10                  15

Lys Thr Pro Asn Asn Asp Lys Ser Leu Val Lys Thr
            20                  25

<210> SEQ ID NO 3
<211> LENGTH: 446
<212> TYPE: PRT
<213> ORGANISM: Plasmodium falciparum

<400> SEQUENCE: 3

Met Ala His Val Ile Thr Arg Ile Asn Ala Arg Glu Ile Leu Asp Ser
1               5                   10                  15

Arg Gly Asn Pro Thr Val Glu Val Asp Leu Glu Thr Asn Leu Gly Ile
            20                  25                  30

Phe Arg Ala Ala Val Pro Ser Gly Ala Ser Thr Gly Ile Tyr Glu Ala
            35                  40                  45

Leu Glu Leu Arg Asp Asn Asp Lys Ser Arg Tyr Leu Gly Lys Gly Val
    50                  55                  60

Gln Lys Ala Ile Lys Asn Ile Asn Glu Ile Ile Ala Pro Lys Leu Ile
65                  70                  75                  80

Gly Met Asn Cys Thr Glu Gln Lys Lys Ile Asp Asn Leu Met Val Glu
                85                  90                  95

Glu Leu Asp Gly Ser Lys Asn Glu Trp Gly Trp Ser Lys Ser Lys Leu
            100                 105                 110

Gly Ala Asn Ala Ile Leu Ala Ile Ser Met Ala Val Cys Arg Ala Gly
            115                 120                 125

Ala Ala Ala Asn Lys Val Ser Leu Tyr Lys Tyr Leu Ala Gln Leu Ala
        130                 135                 140

Gly Lys Lys Ser Asp Gln Met Val Leu Pro Val Pro Cys Leu Asn Val
145                 150                 155                 160

Ile Asn Gly Gly Ser His Ala Gly Asn Lys Leu Ser Phe Gln Glu Phe
                165                 170                 175

Met Ile Val Pro Val Gly Ala Pro Ser Phe Lys Glu Ala Leu Arg Tyr
            180                 185                 190

Gly Ala Glu Val Tyr His Thr Leu Lys Ser Glu Ile Lys Lys Lys Tyr
        195                 200                 205

Gly Ile Asp Ala Thr Asn Val Gly Asp Glu Gly Gly Phe Ala Pro Asn
    210                 215                 220

-continued

```
Ile Leu Asn Ala Asn Glu Ala Leu Asp Leu Leu Val Thr Ala Ile Lys
225                 230                 235                 240

Ser Ala Gly Tyr Glu Gly Lys Val Lys Ile Ala Met Asp Val Ala Ala
            245                 250                 255

Ser Glu Phe Tyr Asn Ser Glu Asn Lys Thr Tyr Asp Leu Asp Phe Lys
            260                 265                 270

Thr Pro Asn Asn Asp Lys Ser Leu Val Lys Thr Gly Ala Gln Leu Val
            275                 280                 285

Asp Leu Tyr Ile Asp Leu Val Lys Lys Tyr Pro Ile Val Ser Ile Glu
            290                 295                 300

Asp Pro Phe Asp Gln Asp Asp Trp Glu Asn Tyr Ala Lys Leu Thr Ala
305                 310                 315                 320

Ala Ile Gly Lys Asp Val Gln Ile Val Gly Asp Asp Leu Leu Val Thr
            325                 330                 335

Asn Pro Thr Arg Ile Thr Lys Ala Leu Glu Lys Asn Ala Cys Asn Ala
            340                 345                 350

Leu Pro Leu Lys Val Asn Gln Ile Gly Ser Ile Thr Glu Ala Ile Glu
            355                 360                 365

Ala Cys Leu Leu Ser Gln Lys Asn Asn Trp Gly Val Met Val Ser His
            370                 375                 380

Arg Ser Gly Glu Thr Glu Asp Val Phe Ile Ala Asp Leu Val Val Ala
385                 390                 395                 400

Leu Arg Thr Gly Gln Ile Lys Thr Gly Ala Pro Cys Arg Ser Glu Arg
            405                 410                 415

Asn Ala Lys Tyr Asn Gln Leu Leu Arg Ile Glu Glu Ser Leu Gly Asn
            420                 425                 430

Asn Ala Val Phe Ala Gly Glu Lys Phe Arg Leu Gln Leu Asn
            435                 440                 445

<210> SEQ ID NO 4
<211> LENGTH: 434
<212> TYPE: PRT
<213> ORGANISM: Homo sapiens

<400> SEQUENCE: 4

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
        50                  55                  60

Ala Val Glu His Ile Asn Lys Thr Ile Ala Pro Ala Leu Val Ser Lys
65              70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Ser Glu Val Ile
            130                 135                 140

Leu Pro Val Pro Ala Phe Asn Val Ile Asn Gly Gly Ser His Ala Gly
```

```
                145                 150                 155                 160
Asn Lys Leu Ala Met Gln Glu Phe Met Ile Leu Pro Val Gly Ala Ala
                    165                 170                 175

Asn Phe Arg Glu Ala Met Arg Ile Gly Ala Glu Val Tyr His Asn Leu
                    180                 185                 190

Lys Asn Val Ile Lys Glu Lys Tyr Gly Lys Asp Ala Thr Asn Val Gly
                    195                 200                 205

Asp Glu Gly Gly Phe Ala Pro Asn Ile Leu Glu Asn Lys Glu Gly Leu
                    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                    245                 250                 255

Tyr Asp Leu Asp Phe Lys Ser Pro Asp Pro Ser Arg Tyr Ile Ser
                    260                 265                 270

Pro Asp Gln Leu Ala Asp Leu Tyr Lys Ser Phe Ile Lys Asp Tyr Pro
                    275                 280                 285

Val Val Ser Ile Glu Asp Pro Phe Asp Gln Asp Asp Trp Gly Ala Trp
                    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                    325                 330                 335

Cys Asn Cys Leu Leu Leu Lys Val Asn Gln Ile Gly Ser Val Thr Glu
                    340                 345                 350

Ser Leu Gln Ala Cys Lys Leu Ala Gln Ala Asn Gly Trp Gly Val Met
                    355                 360                 365

Val Ser His Arg Ser Gly Glu Thr Glu Asp Thr Phe Ile Ala Asp Leu
                    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                    405                 410                 415

Leu Gly Ser Lys Ala Lys Phe Ala Gly Arg Asn Phe Arg Asn Pro Leu
                    420                 425                 430

Ala Lys

<210> SEQ ID NO 5
<211> LENGTH: 29
<212> TYPE: PRT
<213> ORGANISM: Artificial sequence
<220> FEATURE:
<223> OTHER INFORMATION: Synthetic antigen

<400> SEQUENCE: 5

Glu Glu Glu Glu Glu Ala Ser Glu Phe Tyr Asn Ser Glu Asn Lys Thr
1               5                   10                  15

Tyr Asp Leu Asp Phe Lys Thr Pro Asn Asn Asp Gly Gly
            20                  25

<210> SEQ ID NO 6
<211> LENGTH: 29
<212> TYPE: PRT
<213> ORGANISM: Artificial sequence
<220> FEATURE:
<223> OTHER INFORMATION: Synthetic antigen
```

<400> SEQUENCE: 6

Glu Glu Glu Glu Glu Ala Ser Glu Phe Tyr Asn Ser Glu Asn Lys Thr
1               5                   10                  15
Tyr Asp Leu Asp Phe Lys Thr Pro Asn Asn Asp Pro Gly
            20                  25

<210> SEQ ID NO 7
<211> LENGTH: 30
<212> TYPE: PRT
<213> ORGANISM: Artificial sequence
<220> FEATURE:
<223> OTHER INFORMATION: Synthetic antigen

<400> SEQUENCE: 7

Glu Glu Glu Glu Glu Ala Ser Glu Phe Tyr Asn Ser Glu Asn Lys Thr
1               5                   10                  15
Tyr Asp Leu Asp Phe Lys Thr Pro Asn Asn Asp Pro Gly Cys
            20                  25                  30

<210> SEQ ID NO 8
<211> LENGTH: 6
<212> TYPE: PRT
<213> ORGANISM: Artificial sequence
<220> FEATURE:
<223> OTHER INFORMATION: Synthetic antigen

<400> SEQUENCE: 8

Lys Glu Glu Glu Glu Cys
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic antigen

<400> SEQUENCE: 9

Lys Glu Glu Glu Glu Cys Lys
1               5

<210> SEQ ID NO 10
<211> LENGTH: 11
<212> TYPE: PRT
<213> ORGANISM: Plasmodium falciparum

<400> SEQUENCE: 10

Val Ala Ala Ser Glu Phe Tyr Asn Ser Glu Lys
1               5                   10

<210> SEQ ID NO 11
<211> LENGTH: 11
<212> TYPE: PRT
<213> ORGANISM: Plasmodium falciparum

<400> SEQUENCE: 11

Phe Tyr Asn Ser Glu Asn Lys Thr Tyr Asp Lys
1               5                   10

<210> SEQ ID NO 12
<211> LENGTH: 11
<212> TYPE: PRT
<213> ORGANISM: Plasmodium falciparum

<400> SEQUENCE: 12

```
Asn Lys Thr Tyr Asp Leu Asp Phe Lys Thr Lys
1               5                   10

<210> SEQ ID NO 13
<211> LENGTH: 10
<212> TYPE: PRT
<213> ORGANISM: Plasmodium falciparum

<400> SEQUENCE: 13

Leu Asp Phe Lys Thr Pro Asn Asn Asp Lys
1               5                   10

<210> SEQ ID NO 14
<211> LENGTH: 11
<212> TYPE: PRT
<213> ORGANISM: Plasmodium falciparum

<400> SEQUENCE: 14

Pro Asn Asn Asp Lys Ser Leu Val Lys Thr Lys
1               5                   10

<210> SEQ ID NO 15
<211> LENGTH: 11
<212> TYPE: PRT
<213> ORGANISM: Plasmodium falciparum

<400> SEQUENCE: 15

Ser Leu Val Lys Thr Gly Ala Gln Leu Val Lys
1               5                   10

<210> SEQ ID NO 16
<211> LENGTH: 25
<212> TYPE: PRT
<213> ORGANISM: Plasmodium falciparum

<400> SEQUENCE: 16

Val Ala Ala Ser Glu Phe Tyr Asn Ser Glu Asn Lys Thr Tyr Asp Leu
1               5                   10                  15

Asp Phe Lys Thr Pro Asn Asn Asp Lys
            20                  25

<210> SEQ ID NO 17
<211> LENGTH: 36
<212> TYPE: PRT
<213> ORGANISM: Plasmodium falciparum

<400> SEQUENCE: 17

Val Ala Ala Ser Glu Phe Tyr Asn Ser Glu Asn Lys Thr Tyr Asp Leu
1               5                   10                  15

Asp Phe Lys Thr Pro Asn Asn Asp Lys Ser Leu Val Lys Thr Gly Ala
            20                  25                  30

Gln Leu Val Lys
        35

<210> SEQ ID NO 18
<211> LENGTH: 5
<212> TYPE: PRT
<213> ORGANISM: Plasmodium falciparum

<400> SEQUENCE: 18

Lys Ser Leu Val Lys
1               5
```

```
<210> SEQ ID NO 19
<211> LENGTH: 28
<212> TYPE: PRT
<213> ORGANISM: Streptococcus pneumoniae

<400> SEQUENCE: 19

Cys Ala Ser Ser Glu Phe Tyr Asp Lys Glu Arg Lys Val Tyr Asp Tyr
1               5                   10                  15

Thr Lys Phe Glu Gly Glu Gly Ala Ala Val Arg Thr
            20                  25

<210> SEQ ID NO 20
<211> LENGTH: 32
<212> TYPE: PRT
<213> ORGANISM: Homo sapiens

<400> SEQUENCE: 20

Val Ala Ala Ser Glu Phe Phe Arg Ser Gly Lys Tyr Asp Leu Asp Phe
1               5                   10                  15

Lys Ser Pro Asp Asp Pro Ser Arg Tyr Ile Ser Pro Asp Gln Leu Ala
            20                  25                  30

<210> SEQ ID NO 21
<211> LENGTH: 35
<212> TYPE: PRT
<213> ORGANISM: Plasmodium falciparum

<400> SEQUENCE: 21

Val Ala Ala Ser Glu Phe Tyr Asn Ser Glu Asn Lys Thr Tyr Asp Leu
1               5                   10                  15

Asp Phe Lys Thr Pro Asn Asn Asp Lys Ser Leu Val Lys Thr Gly Ala
            20                  25                  30

Gln Leu Val
        35
```

ARTIFICIAL ANTIGEN PRODUCED USING PARTIAL SEQUENCE OF ENOLASE PROTEIN ORIGINATED FROM PLASMODIUM FALCIPARUM, AND METHOD FOR PRODUCING SAME

CROSS-REFERENCE TO RELATED APPLICATIONS

This patent application is the U.S. national phase of International Patent Application No. PCT/JP2015/083437, filed Nov. 27, 2015, which claims the benefit of Japanese Patent Application No. 2014-241420, filed on Nov. 28, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,598 bytes ASCII (Text) file named "728645Sequence-Listing.txt," created May 26, 2017

TECHNICAL FIELD

The present invention relates to a novel bioactive peptide and the use thereof. Further, the present invention relates to: an antigen for immunization, which is characterized by including a partial amino acid sequence of enolase derived from a malaria parasite, which utilizes an immune reaction thereto in humans and other animals, and which inhibits the proliferation of the malaria parasite; and a pharmaceutical composition and a material for use in an antibody titer test, including the same.

BACKGROUND ART

Prior Arts and Problems Thereof (1) Current Status of Malaria as Infectious Disease WHO, the World Health Organization, has stated in its latest report that malaria is prevalent in 103 countries around the world, and that the numbers of affected individuals and fatalities in 2012 are estimated to be 207 million and 627 thousand, respectively [Non-patent Document 1]. Most of the cases (80%) and fatalities (90%) reported are those from African region. Further, 77% of the fatalities are children under 5 years old. Global scale measures taken in recent years served to significantly reduce the number of affected individuals (29%) and fatalities (45%) by 2012, as compared to the data in 2000. This has been regarded as an achievement of positive actions, such as distribution of effective drugs and mosquito nets, taken by international organizations such as WHO and Global Fund, and government and non-government organizations including that of Japan. However, malaria endemic areas still remain in countries with growing economies, such as India, Brazil, Thailand, Malaysia, and China. In addition, the world is now facing problems of emergence and proliferation of drug-resistant malaria parasites. Thus, malaria still remains one of the major infectious diseases.

In Japan, malaria is designated as "infectious diseases Category IV" and it is obligated by law to report all cases. Indigenous malaria in Japan had been controlled, with the case in Hikone in 1959 being the last case. However, the economic growth in Japan has significantly increased the mobility of people, and as a result, there has been a rapid increase since 1980s in the number of cases in Which Japanese passengers are infected with malaria in endemic areas, and cases of so-called "imported malaria" in which entrants from endemic areas to Japan develop malaria in Japan [Non-patent Document 2]. Although 154 cases have been reported in 2000, which was the highest number ever, annually reported eases are now within the range of from 50 to 60, due to increased knowledge of passengers regarding malaria prevention.

In neighboring South Korea, "indigenous malaria" which had once been controlled re-emerged in 1993. The reported cases have increased up to 4,000 cases in 2000, but decreased to 394 cases by 2012 [Non-patent Document 3]. The cases of imported malaria from South Korea to Japan have also been reported [Non-patent Document 4]. In view of the facts that: the major species of mosquito which transmit vivax malaria in South Korea is Chinese anopheles (*Anopheles sinensis*), which is the same as that in Japan; there are a large passenger flow and physical distribution between Japan and South Korea; and malaria remained uncontrolled in South Korea for 20 years; there is a serious concern regarding the influx of malaria parasites and vector mosquitoes in South Korea into Japan. Therefore, taking preventive measures for malaria is extremely important, not only in endemic areas, but also for controlling epidemics in Japan.

Further, malaria is not only a health issue, but also a cause for stagnation in economy and social unrest in African countries. It has been pointed out that a recent increase in infected individuals in endemic areas is related to exploitation of tropical rainforest and global warming. According to the Intergovernmental Panel on Climate Change report ("Special Report: Global Warming of 1.5° C.," 1996 and 1998), a 2° C. increase in temperature due to global warming is predicted to result in an increase of 50 to 80 million affected individuals. Accordingly, there is a concern for the resurgence of malaria, even in the temperate regions, including Japan, in which malaria is thought to have been eradicated by the dissemination of DDT and hygiene measures after the World War II.

(2) Species and life history of malaria parasites:

Malaria is a parasitic infection caused by malaria parasite genus (genus *Plasmodium*). There are following four species of malaria parasites which infect humans: *falciparum* malaria parasite (*P. falciparum*); vivax malaria parasite (*P. vivax*); quartan malaria parasite (*P. malariae*); and *ovale* malaria parasite (*P. ovald*). Among these, *P. falciparum* has the highest virulence, and induces severe symptoms such as severe anemia and cerebral malaria, causing death in patients, in some cases.

Further, it was reported in 2004 that humans have been infected with one species of simian malaria (*P. knowlesi*) in wide areas in South East Asia, and *P. knowlesi* is now starting to be recognized as the fifth malaria parasite capable of infecting humans [Non-patent Document 5]. Cases of imported infection in Japan have also been reported [on-patent Document 6]. Recent exploitation of tropical rainforest is also considered as one of the causes for simian malaria infection. Further, about 60 species of genus *Anopheles* are known to transmit malaria parasites to humans.

(3) Infection Route of Malaria and Life Cycle of Malaria Parasites:

Malaria is caused by invasion of malaria parasites into the body of an individual, due to the individual being bitten by a female *Anopheles*. The life cycle of malaria parasites is categorized into two stages: one during which the parasites reside in the body of a mosquito, and one in the body of a human. When a mosquito carrying malaria parasites sucks blood from a human, infectious sporozoites (intrahepatic sporozoites) present in the salivary gland of the mosquito enter the blood stream of the human, and rapidly migrate to the liver. The sporozoites rapidly divide within liver cells to generate multinuclear schizonts. Numerous merozoites (intraerythrocytic merozoites) are then released from mature schizonts into the blood stream, and invade red blood cells. The merozoites divide inside red blood cells, while transforming through ring-forms, trophozoites (mature trophozoites), and schizonts. A single merozoite produces 8 to 32 new merozoites within 48 to 72 hours, depending on the species of the parasite. When merozoites are matured, at this stage, the merozoites destroy red blood cells and are released into the blood stream, and then invade new red blood cells. This erythrocytic cycle will be repeated thereafter. An infected individual presents symptoms of malaria, such as fever and chill, triggered by the destruction of red blood cells and release of merozoites. Some of the released merozoites differentiate into dioecious gametocytes, and survive in the blood stream for a long period of time.

When a mosquito sucks blood from the infected individual, the gametocytes enter the body of the mosquito, and then transform into male and female gametes inside the mid-gut of the mosquito. Male and female gametes fuse to form ookinetes, and then differentiate into oocysts. Subsequently, several thousands of sporozoites which have rapidly proliferated inside the oocysts are released from the mid-gut wall of the mosquito, due to destruction of oocysts, and migrate to the salivary gland. This infection cycle continues as the mosquito sucks blood and thereby infects another human. In the case of *P. vivax* and *P. ovald*, it is characteristic that hypnozoites are formed in the liver of an infected human, and the disease relapses one to several months, or one or more years in some cases, after the infection.

(4) Various Types of Therapeutic Agents and Drug-Resistant Malaria:

Most of the pre-existing antimalarial drugs act during the blood-stage. Chloroquine has long been administered as a specific remedy for malaria, before and after the Word War II. However, Chloroquine-resistant *P. falciparum* have spread around the world since 1950s, and the usefulness of the drug has been significantly reduced. In particular, *P. falciparum* with high chloroquine-resistance has been found in Thailand and neighboring countries, Oceania, the Amazon River Basin in Brazil, and East Africa. Pyrimethamine is used in combination with sulfadoxine, and the cases highly resistant to these drugs have been reported in the Amazon River Basin and South East Asia. Cases of mefloquine-resistant malaria are frequently found in Thailand, and the border region between Cambodia and Myanrriar, and the cases in the Amazon River Basin and Africa have also been reported. Although quinine has conventionally been effective for treating multiple-drug-resistant malaria, there are reports from South East Asia and Brazil that the susceptibility to the drug is decreasing. The emergence of chloroquine-resistant *P. vivax* has also been reported. In addition, the cases of *P. vivax* resistant to treatment with primaquine, which is a pharmaceutical capable of killing hypnozoites lying dormant in the liver of an infected individual, have also been reported [Non-patent Document 7].

(5) Standard Therapeutic Agents for Malaria:

In the case of *falciparum* malaria infection, a delay in treatment increases the severity of the disease (except for the residents in endemic areas), it is essential that the treatment with an appropriate antimalarial drug be administered swiftly. Standard treatment aims to kill malaria parasites in red blood cells in the peripheral blood, and to prevent fever in the acute stage of infection, thereby ameliorating the clinical symptoms. However, there are only four types of antimalarial drugs which have been approved in Japan. Specifically, the four types of antimalarial drugs are: (1) mefloquine hydrochloride and (2) a combination of atovaquone/ proguanil hydrochloride, which are currently available and can be easily used; (3) a combination of sulfadoxine/ pyrimethamine, which are not currently in the market; and (4) a quinine oral drug, whose prescription protocol is complicated. For the treatment of *falciparum* malaria patients who are considered to have been infected in the region where the above described drug-resistant *P. falciparum* have been found, (5) a combination of artemether/ lumefantrine, or (2) a combination of atovaquone/proguanil are administered.

For the treatment of vivax malaria and *ovale* malaria infection, (6) chloroquine can be the first choice drug. However, a fundamental therapeutic agent for preventing relapse is further required. In other words, malaria parasites in the stage called hypnozoites, which lie dormant in the liver cells of a patient, do not respond to the drugs aimed at parasites in the erythrocytic stage, and thus it is necessary to additionally administer primaquine which is capable of specifically killing the intrahepatic parasites. There have been many reports that vivax malaria in Papua New Guinea and the neighboring regions in the southern hemisphere is less susceptible to primaquine, and thus the administration of double doses is recommended. Further, since primaquine has a strong side effect of inducing intravascular hemolysis in a patient with G6PD deficiency, it is necessary to examine the enzyme activity of G6PD before the administration.

(6) Necessity of Vaccines and Problems in Vaccine Development:

As described above, a novel therapeutic agent for malaria is always associated with the problems of the emergence and proliferation of the drug-resistant malaria parasites. Therefore, development of vaccines is desired as a promising alternative for the prevention of malaria infection. In particular, the development and study of vaccines against *falciparum* malaria, which could cause death in severe cases, have been done around the world. The development had begun in 1980s, but none of the vaccines have yet reached the stage of practical use. One of the reasons for this is the recently discovered fact that malaria parasites have evolved to obtain a mechanism of parasite adaptation, which allows them to evade the protective immune system of humans. Thus, it is now known that malaria is significantly different from a "one-time infection", such as measles or smallpox, to which a person can acquire protective immunity by being administered with a vaccine, or by being infected once. It has been clarified that the mechanism to evade the immune system is related to the complex life history of malaria parasites which go through a variety of morphological changes (target antigens also change accordingly), and also to the formation of multigene families and the presentation of genetic polymorphism [Non-patent Document 8].

A well-known example of the multigene families is PfEMP-1 protein which is present in "knob" formed on the surfaces of red blood cells infected with *P. falciparum*, and a single malaria parasite carries an extremely large number of copies of the protein [Non-patent Documents 9 and 10]. In other words, since different copies of the protein are presented on the surfaces of red blood cells, at every new cycle of the intraerythrocytic cycle, it is difficult for the immune system to target and attack the protein. An example of the polymorphism is MSP1, which is a membrane protein present on the surfaces of merozoites [Non-patent Documents 11 and 12]. In this case, although a single malaria parasite carries only one copy of the MSP1 protein, the protein in each of the parasites has a different sequence, and thus, the protective immunity against MSP1 acquired in the initial infection does not work in the next infection.

(7) Development of Malaria Vaccines Carried Out So Far:

"Sporozoites" which entered the body of an individual who had been bitten by an *Anopheles* mosquito that transmits malaria parasite, swiftly migrate through the blood stream to liver cells, and then first proliferate in the liver cells (intrahepatic stage). Subsequently, "merozoites" released into the blood stream invade red blood cells and proliferate repeatedly (intraerythrocytic stage). Some of the proliferated parasites transform into male and female "gametocytes" and continues to infect other humans by the blood-sucking of *Anopheles* mosquitoes (mosquito stage). Efforts are being made for the development and study of vaccines targeting the respective stages in the life history of the malaria parasites [Non-patent Documents 13 and 14].

The world's first clinical study of a malaria vaccine had been done by Patarroyo et. al. in Colombia, using a chemically synthesized peptide antigen of 44 residues, called SPf66 [Non-patent Document 15]. SPf66 was used in trial in endemic areas in Asia and Africa, but failed to prove sufficient efficacy.

Thereafter, clinical trials of various types of vaccine candidates have been done. Currently, the most advanced vaccine development program is that of RTS, S/AS01, developed by GlaxoSmithKline Inc. (GSK), and the world's first, large-scale phase III clinical trial had been carried out. In October, 2010, the interim progress report that RTS, S/AS01 reduced the risk of infection to half the previous level in one to five-year old infants and toddlers in Africa, had become big news [Non-patent Document 16]. However, the final report issued in November, 2012 concluded that the vaccine demonstrated an efficacy ratio of 31% in the prevention against malaria infection, and an efficacy ratio of 37% in the treatment of severe cases of malaria, with respect to 3,200 infants and toddlers involved in the trial. In other words, even the most advanced vaccine, RTS, S/AS01 was proven to have an efficacy ratio of only about 30% [Non-patent Document 17].

In Japan, the clinical trial of SE36/AHG vaccine, developed by Horii et. al. of Osaka University, had been carried out in Japan (2005) and in endemic areas in Uganda (from April, 2010 to February, 2011) [Non-patent Document 18].

Most of the clinical development programs of malaria vaccines hitherto carried out [Non-patent Document 19] employed a method in which a recombinant protein antigen is directly administered to a human subject, so as to allow the human immune system to produce antibodies against the antigen. Examples of antibody targets include: (1) a sporozoite surface antigen (CSP) (for preventing parasite invasion into liver cells); (2) a merozoite surface antigen (MSP1) (for preventing parasite invasion into red blood cells); (3) an infected erythrocyte surface antigen (PfEMP-1, SERA-5) (for inhibiting parasite proliferation within red blood cells); (4) a transmission-blocking antigen (for preventing parasite invasion into the mid-gut, and/or inhibiting parasite proliferation, in the body of a mosquito); and the like. Further, examples of the vaccine include: (5) a DNA vaccine using an attenuated adenovirus, which expresses an antigen inside the body; and (6) a live vaccine, obtained by attenuating parasites by irradiation or genetic engineering. Still further, examples thereof also include: (7) a "multi-stage vaccine" obtained by linking a plurality of parasite antigens; and (8) a "prime-boost vaccine" obtained by artificially combining a plurality of vaccine candidates.

(8) Current Status of Development of Pharmaceutical Composition for Use as Malaria Vaccine Using Enolase:

It is known, according to the epidemiological surveys of malaria, that most of the fatalities are "infants and toddlers in endemic areas" and "passengers from non-endemic areas, such as Japanese". On the other hand "adults in endemic areas" are more likely to recover, even when infected with malaria. The reason for this is thought to be that the residents in endemic areas "have acquired and are maintaining immunity to malaria, due to persistent infection with malaria". Thus, it is evident that the vaccine development must be done taking into consideration individual differences in immune status.

During the course of an epidemiologic study, Suzuki and Kano of the medical department of Gunma University have discovered that *P. falciparum*-derived enolase, a glycolytic enzyme, is a common antigen molecule involved in the improvement in the pathological condition of *falciparum* malaria patients in the acute stage, based on a field survey in endemic areas in South America and South East Asia [Non-patent Document 20]. In other words, they have found out that enolase, a glycolytic enzyme, produced by *P. falciparum* which have infected humans, functions as an immune molecule against *P. falciparum*, and started the development of a vaccine using the enolase [Non-patent Documents 21 and 22].

The vaccine antigen using enolase is a vaccine based on a concept which takes into consideration individual differences in immune status, and thus is clearly distinguished from conventional vaccines based solely on data obtained in laboratories. Thus, although a vaccine study using *P. falciparum* enolase as an antigen has been recently carried out [Non-patent Document 23], it can be easily understood that the origin of the idea of the present inventors significantly differs in the research direction, from the development of vaccine antigens carried out so far.

To begin the vaccine development, the present inventors have first studied the molecular design and the chemical synthesis of a recombinant enolase including an amino acid sequence derived from *P. falciparum*, and antigen peptides using partial amino acid sequences of *P. falciparum* enolase. Examples include AD22 sequence (Ala256 to Asp277) (SEQ ID NO: 1) and AT28 sequence (Ala256 to Thr283) (SEQ ID NO: 2). An immunological study using the above described enolase and artificial antigen peptide sequences revealed that an anti-enolase antibody and anti-peptide antibodies prepared by immunizing a rabbit inhibit the proliferation of *P. falciparum* in vitro [Patent Document 1].

Subsequently, a vaccine trial was carried out using as antigens enolase derived from *P. falciparum* and an AD22 partial sequence peptide, and using 13 owl monkeys. The changes in the percentage of parasitism of *P. falciparum* in red blood cells in the peripheral blood of the owl monkeys were plotted. As a result, a rapid increase in the percentage of parasitism was in inhibited in the owl monkeys administered with the vaccine, revealing an excellent efficacy as a vaccine. Further, it has also been found out that the production of antibodies which immunologically react with the parasite enolase was induced by any of the antigens.

The antigen which causes owl monkeys to acquire immunity is a chemically synthesized peptide antigen having a tandem structure in which four 22-residue peptides (AD22) are tandemly arranged, and has a structure represented by the following Structural Formula (A). Although Xaa in the Structural Formula (A) of the antigen is arbitrary, a Cys (Acm) residue, which is a Cys residue whose side chain is protected by an acetamidomethyl group, is used at this time.

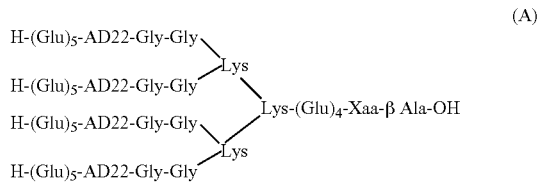

(A)

Further, the inventors studied the processing of the AD22 antigen peptide, from the viewpoint of chemical synthesis, and have successfully developed a fragment condensation method which is suitable for mass synthesis [Patent Document 2]. In other words, they have found out a method which allows for a large-scale synthesis of a peptide of interest which includes partial sequences of *P. falciparum* enolase, or an analogue thereof, by condensing five short-chain peptide segments to form one protected peptide chain.

In addition, the research group of the present inventors started the development of a novel pharmaceutical composition, as a vaccine which is based on epidemiological findings. The residents in endemic areas of malaria are known to maintain a protective immune status due to repeatedly infected with malaria parasites. Therefore, the research group has developed an artificial antigen material capable of controlled and sustained release of an antigen, in order to reproduce the immune status of the residents in endemic areas, using a technique of materials chemistry. Specifically, they have found out a method for preparing antigen nanoparticles obtained by encapsulating AD22 antigen peptides within biodegradable microparticles, and immunologically superior properties of the particles [Patent Document 3]. Further, the research group has also reported peptide-presenting microparticles obtained by introducing an antigen peptide into a polymer [Patent Document 4].

As described above, the long-standing efforts of the present inventors has finally started to unravel the usefulness of the partial sequences of *P. falciparum* enolase, and of the AD22 sequence in particular, as vaccine antigens. The next problem to be solved was that, in the case of using the AD22 sequence as a peptide antigen, it was necessary to synthesize the antigen peptide so as to satisfy the standards for pharmaceuticals.

(9) Investigation of Synthesis Method of AD22 Antigen Peptide:

In order to incorporate the AD22 sequence, which is a partial structure of *P. falciparum* enolase, or an analogue thereof, into a pharmaceutical which can be administered to a human, it is required that the molecular structure and the production method thereof are compatible with specification setting for a GMP-compliant production process, which is required for pharmaceuticals. In particular, it is required to establish quality standards (mass spectrometry analysis, HPLC analysis, analysis of impurities and analogues, and the like) which are compliant with the guidelines for drug substances of chemically synthesized products.

First, a peptide antigen having a structure represented by the above described Structural Formula (A) was produced by a synthesis method suitable for a pharmaceutical production. In general, the production of the peptide antigen can be easily carried out by allowing condensation reactions of Fmoc protected amino acids to proceed from the C terminus, successively. However, as shown in the following scheme, the present inventors synthesized the peptide antigen by fragment condensation of: linear sequence fragments ($E_5$-AD22-$G_2$: SEQ ID NO: 5), each produced by Fmoc method and including the AD22 antigen, and a Lys branching segment, via amide bonds. This method is advantageous in that the analysis of impurities and analogues in the drug substance can be easily performed, since each of the peptide fragments is sufficiently purified before carrying out the synthesis.

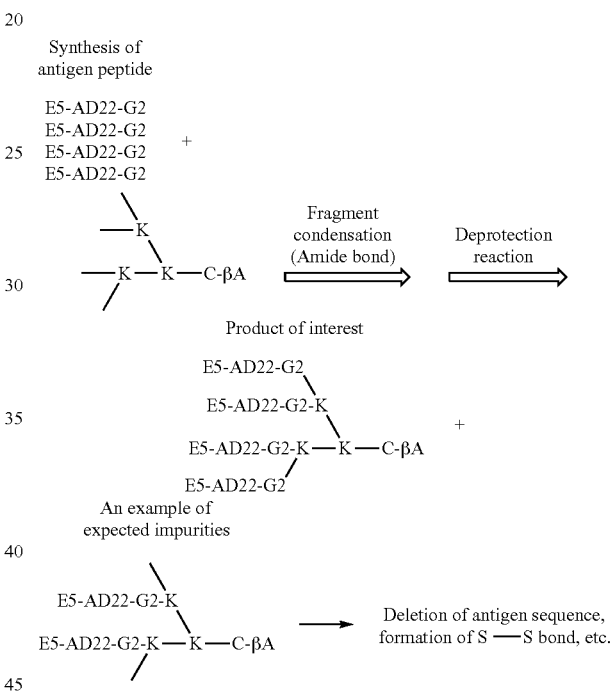

The present inventors carried out the synthesis such that 50 mg of a product of interest can be obtained per lot, and repeated the synthesis process three times, thereby succeeded in obtaining a substance corresponding to the product of interest. However, it was difficult to perform the confirmation test of the thus synthesized antigen peptide by mass spectrometry analysis, GPC analysis, and the like (FIG. 1). In other words, it was revealed that the molecular structure of the peptide antigen needs to be changed to a completely new molecular structure which is suitable for the specification setting (analysis methods) used in a GMP-compliant production process, in order to incorporate the AD22 sequence, which is a partial structure of *P. falciparum* enolase, or an analogue thereof, into a pharmaceutical which can be administered to a human.

(10) Action of Plasminogen Due to Infectious Disease

Enolase is a ninth enzyme in the glycolytic pathway, and plays a role in intracellular energy production. In the case of infection with pathogenic microorganisms such as *Streptococcus pneumoniae*, it has attracted attention that enolase facilitates the infection of host cells by binding to a fibrinolytic protein (plasminogen, tissue plasminogen activator tPA) of a human, on the cell surface [Non-patent Document 24].

In the case of malaria infection, it has been reported that, when malaria parasites reside in the body of a vector mosquito in the form called ookinetes, enolase on the cell surface facilitates the invasion of the parasites into the mid-gut cells of the mosquito [Non-patent Document 25].

Plasminogen is usually contained in plasma, and is activated by binding to a receptor protein. Plasminogen is a protein consisting of 791 residues, and one plasminogen includes five kringle domains and a serine protease domain. The kringle domain is composed of about 80 amino acids, and has a distinctive secondary structure including three sets of S—S crosslinking. The binding of the receptor protein to the kringle domain causes the hydrolysis of the plasminogen activator site, to result in the development of plasmin activity. In recent years, it has been reported that enolase on the cell surface functions as a receptor protein, in various types of pathogenic microorganisms, and thus involved in facilitating the infection of host cells [Non-patent Document 26].

PRIOR ART DOCUMENTS

Patent Documents

Patent Document 1: JP 2002-371098 A
Patent Document 2: WO 2006/035815
Patent Document 3: JP 2009-256324 A
Patent Document 4: JP 2012-240940 A Non-Patent Documents Non-patent Document 1: WHO. Impact of malaria control. World Malaria Report 2013. Geneve: WHO Press, 2013: 55-68.
Non-patent Document 2: Kano S. and Kimura M., Acta Tropica, 89(3):271-278, 2004,
Non-patent Document 3: WHO. Country Profiles (Republic of Korea), World Malaria Report 2013. Geneve: WHO Press, 2013: 165-166.
Non-patent Document 4: Iwagami M, Itoda I, Hwang S Y, Kho W G, Kano S. *Plasmodium vivax* PCR genotyping of the first malaria case imported from South Korea into Japan. J Infect Chemother. 15(1): 27-33, 2009.
Non-patent Document 5: Singh B, Kim Sung L, Matusop A, Radhakrishnan A, Shamsul S S, Cox-Singh J, Thomas A, Conway D J. A large focus of naturally acquired *Plasmodium knowlesi* infections in human beings. Lancet. 363 (9414):1017-1024, 2004.
Non-patent Document 6: Tanizaki R, Ujiie M, Kato Y, Iwagami M, Hashimoto A, Kutsuna S, Takeshita N, Hayakawa K, Kanagawa S, Kano S, Ohmagari N. First case of *Plasmodium knowlesi* infection in a Japanese traveller returning from Malaysia. Malaria J. 12: 128, 2013.
Non-patent Document 7: Shigeyuki Kano. How we can diagnose and treat imported malaria patients in Japan. Modern Media Vol. 57, pp. 299-308, 2011.
Non-patent Document 8: Stanisic D I, Barry A E, Good W. Escaping the immune system: How the malaria parasite makes vaccine development a challenge. Trends Parasitol. 29(12): 612-22, 2013.
Non-patent Document 9: Mercereau-Puijalon O, Fandeur T, Guillotte M, Bonnefoy S. Parasite features impeding malaria immunity: antigenic diversity, antigenic variation and poor immunogenicity. Res Immunol. 142(8):690-697, 1991.

Non-patent Document 10: Craig A, Scherf A. Molecules on the surface of the *Plasmodium falciparum* infected erythrocyte and their role in malaria pathogenesis and immune evasion. Mol Biochem Parasitol. 115(2):129-143, 2001.
Non-patent Document 11: Tanabe K, Sakihama N, Kaneko A. Stable SNPs in malaria antigen genes in isolated populations. Science. 2004, 303, 493.
Non-patent Document 12: Snounou G, Viriyakosol 5, Zhu X P et al. High sensitivity of detection of human malaria parasites by the use of nested polymerase chain reaction. Mol Biochem Parasitol. 61(2):315-320, 1993.
Non-patent Document 13: Hiroyuki Oku, Shigeyuki Kano. Basics of Malaria and Vaccines (Malaria no kiso to wakuchin). The journal of biomedical science and biosafety 26(1):31-35, 2014.
Non-patent Document 14: Hiroyuki Oku, Shigeyuki Kano. Malaria vaccines. Regulatory science of medical products. 2(2): 159-165, 2012.
Non-patent Document 15: Patarroyo M E, Amado R, Clavijo P, Moreno A, Guzman F, Romero P, et al. A synthetic vaccine protects humans against challenge with asexual blood stages of *Plasmodium falciparum* malaria. Nature. 332(6160): 158-161, 1988.
Non-patent Document 16: RTS, S Clinical Trials Partnership. First results of phase 3 trial of RTS,S/AS01 malaria vaccine in African children. New Engl J Med. 365(20): 1863-1875, 2011.
Non-patent Document 17: RTS, S Clinical Trials Partnership. A phase 3 trial of RTS,S/AS01 malaria vaccine in African infants. New Engl J Med. 367(24): 2284-2295, 2012.
Non-patent Document 18: Palacpac N M, Arisue N, Tougan T, Ishii K J, Horii T. *Plasmodium falciparum* serine repeat antigen 5 (SE36) as a malaria vaccine candidate. Vaccine. 29(35): 5837-5845, 2011.
Non-patent Document 19: Crompton P D, Pierce S K, Miller L H. Advances and challenges in malaria vaccine development. J Clin Invest. 120(12): 4168-4178, 2010.
Non-patent Document 20: Kano S, El Gaddal A A, Suzuki M. Clinical and epidemiological studies on a 47 kD *Plasmodium thiciparum* antigen. Jpn J Trop Med Hyg. 18(4): 317-324, 1990.
Non-patent Document 21: Norazmi M K, Kano S, Alias A Abdullah M S, Suzuki M. Reactivity of sera from patients with acute *Plasmodium falciparum* and *P. vivax* infections with an antigen Preparation from a *P. falciparum* isolate: mutually exclusive reactivity with a 47 kD and 29 kD band respectively. Jpn J Trop Med Hyg. 24(4):237-239, 1996.
Non-patent Document 22: Kano S, Onda T, Matsumoto Y, Buchachart K, Krudsood S, Looareesuwan S, Aikawa M, Suzuki M. Serological evaluation of malaria patients in Thailand: antibody response against electrophoresed antigenic polypeptides of *Plasmodium falciparum*. Southeast Asian J Trop Med Public Health. 29(2): 341-343, 1998.
Non-patent Document 23: Pal-Bhowmick I, Mehta M, Coppens I, Sharma S, Jarori G K. Protective properties and surface localization of *Plasmodium falciparum* enolase. Infect Immun. 75(11): 5500-5508, 2007.
Non-patent Document 24: Cork A J, Ericsson D J, Law R H, Casey L W, Valkov E, Bertozzi C, Stamp A, Jovcevski B, Aquilina J A, Whisstock J C, Walker M J, Kobe B. PLoS One. 2015, vol. 10, pp. e0121764.
Non-patent Document 25: Ghosh A K, Coppens I, Gardsvoll Ploug M, Jacobs-Lorena M. *Plasmodium* ookinetes coopt mammalian plasminogen to invade the mosquito midgut. Proc Natl Acad Sci USA. 2011, vol. 108, pp. 17153-17158.

Non-patent Document 26: Raymond B B, Djordjevic S. Veterinary Microbiology. 2015, vol. 178, pp. 1-13.

SUMMARY OF THE INVENTION

Technical Problem

An object of the present invention is to provide an antigen peptide which is for use in a novel malaria vaccine, and which has a molecular structure compatible with a GMP-compliant production process. In particular, it is also an object of the present invention to provide methods which are suitable for producing:
microparticles containing a peptide capable of inducing an immune response against malaria parasites, utilizing an immune reaction to the peptide in humans and other animals, or an analogue thereof; and microparticles containing an antigen for immunization capable of inhibiting the proliferation of *falciparum* malaria parasite (*Plasmodium falciparum*).

Solution to Problem

The present inventors have developed an AD22 antigen peptide having a completely novel molecular structure, and a method for producing the same, in order to provide an antigen peptide which is for use in a novel malaria vaccine, and which is compatible with a GMP compliant production process. As a result of numerous experiments under various conditions, the present inventors have succeeded in the synthesis of an antigen peptide having a completely novel two-branched structure, by binding a peptide including an AD22 antigen sequence to each of two amino groups on a Lys residue.

Surprisingly, although this two-branched peptide is a synthetic peptide having a molecular weight of greater than 15,000, the peptide has been proven to be a substance which is free of problems associated with common peptide antigens. Namely, the peptide satisfies the requirements in: solubility (aqueous solubility >1 mg/mL); HPLC analysis (peak separation on an ODS or a GPC column), and mass spectrometry analysis (full width at half maximum within the range of m/z±5). In other words, it has been confirmed that highly accurate analysis data of the peptide compound according to the present invention can be obtained with a high reproducibility, which data can be used in the specification setting for a pharmaceutical.

By establishing the production method as described above, the inventors finally succeeded in finding out: an antigen peptide which is for use in a novel malaria vaccine, and which has a molecular structure compatible with a GMP-compliant production process; and a method for producing the same.

Specifically, the present invention provides the followings.

[1] A peptide comprising a structure in which two peptides each consisting of (i) an amino acid sequence represented by: A01-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-A02 (SEQ ID NO: 1) or (ii) an amino acid sequence represented by: A03-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Lys-Ser-Leu-Val-Lys-Thr-A04 (SEQ ID NO: 2) are linked by amide bonds between the respective carboxy termini of the two peptides and two amino groups of Lys in a linker peptide represented by the following (iii):

(iii) Lys-A05-Cys-A06
and arranged in the form of a two-forked branch (wherein in the above (i), (ii), and (iii), A01 to A06 each represents an amino acid residue(s) in a number of an arbitrary number including 0).

[2] The peptide according to [1], which is represented by the following (I) or (II):

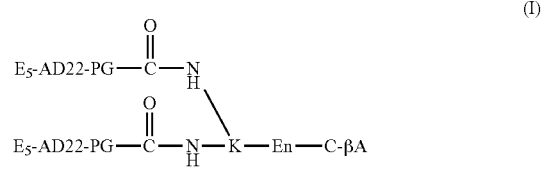

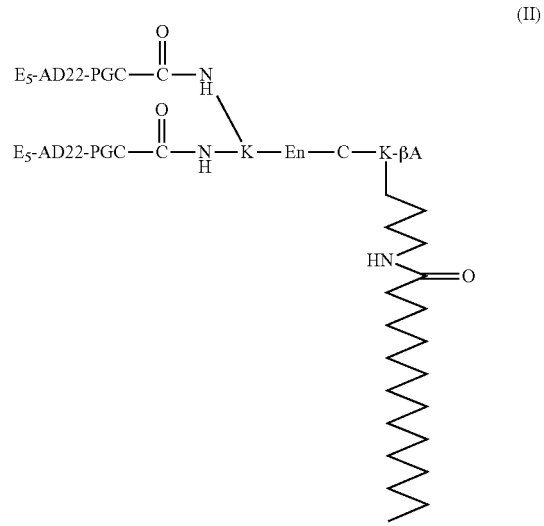

(wherein AD22 represents the amino acid sequence of SEQ ID NO: 1; and n represents an integer of 4 or 5).

[3] A peptide comprising a dimerized structure in which two peptides each according to [1] or [2] are linked by an S—S bond between the Cys residues in the linker peptide sequences, each represented by the above (iii), included in the respective two peptides.

[4] The peptide according to [3], which is represented by the following (I') or (II'):

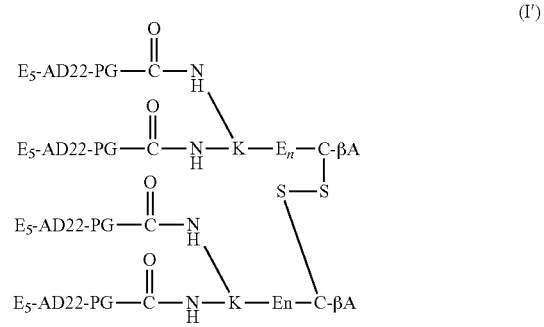

-continued

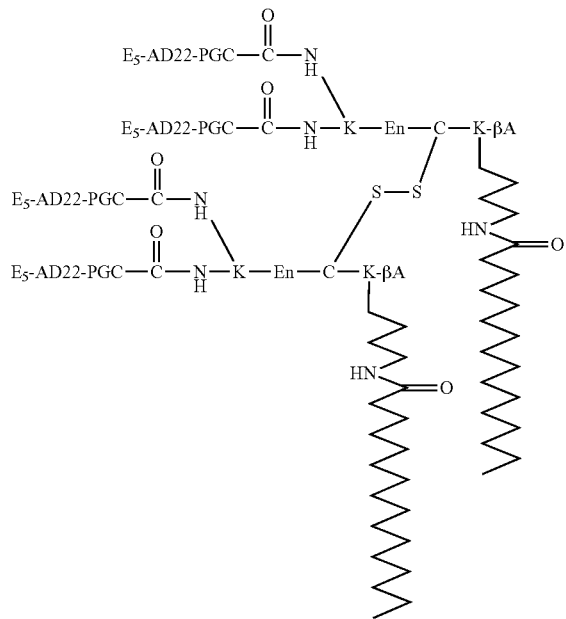

(II')

(wherein AD22 represents the amino acid sequence of SEQ ID NO: 1; and n represents an integer of 4 or 5).

[5] A vaccine for inducing an immune response against malaria, wherein the vaccine comprises the peptide according to any one of [1] to [4].

[6] The vaccine according to [5], for inducing an immune response which blocks or inhibits an interaction between enolase and plasminogen, which interaction is caused by malaria infection.

[7] The vaccine according to [5] or [6], wherein the malaria is malaria caused by an infection with a human or simian malaria parasite.

[8] The vaccine according to [5] or [6], wherein the malaria is malaria caused by an infection with *Plasmodium falciparum*.

[9] The vaccine according to [5] or [6], wherein the malaria is malaria caused by a mixed infection with *Plasmodium falciparum* and another human or simian malaria parasite.

[10] Antigen-comprising microparticles produced by the steps of:
mixing a solution of the peptide according to any one of [1] to [4] with a volatile organic solvent comprising a biodegradable polymer to prepare an emulsion; and
mixing the resulting emulsion with an aqueous solution of a negatively-charged polymer.

[11] The antigen-comprising microparticles according to [10], wherein the biodegradable pot) :ter is a polylactic acid-glycolic acid copolymer.

[12] The antigen-comprising microparticles according to [10], wherein the biodegradable polymer is a polydepsipeptide.

[13] A pharmaceutical composition for preventing or treating a malaria parasite infection (a malaria parasite infectious disease), wherein the composition comprises the antigen-comprising microparticles according to any one of [10] to [12], and a pharmaceutically acceptable carrier.

[14] A substance obtained by allowing the peptide according to any one of [1] to [4] to bind to a solid phase surface of a film, latex particles, ultrafine metal particles or a plastic plate.

[15] A test method for measuring malaria antibody titer in serum or plasma, the method comprising the step of measuring malaria antibody titer in serum or plasma, using the substance according to [14].

[16] A method for analyzing the immune response to the peptide according to any one of [1] to [4], the method comprising the step of measuring an antibody against the peptide according to any one of [1] to [4], using the substance according to [14].

[17] A method for measuring the antibody titer of an individual administered with the peptide according to any one of [1] to [4], the method comprising the step of measuring an antibody against the peptide according to any one of [1] to [4], using the substance according to [14]

[18] A method for producing antigen-comprising microparticles, comprising the steps of:
mixing a solution of the peptide according to any one of [1] to [4] with a volatile organic solvent comprising a biodegradable polymer to prepare an emulsion; and
mixing the resulting emulsion with an aqueous solution of a negatively-charged polymer.

[19] The method for producing antigen-comprising microparticles according to [18], wherein the biodegradable polymer is a polylactic acid-glycolic acid copolymer.

[20] The method for producing antigen-comprising microparticles according to [18], wherein the biodegradable polymer is a polydepsipeptide.

[21] A method for producing a pharmaceutical composition for preventing or treating a malaria parasite infection, the method comprising the steps of:
producing antigen-comprising microparticles by the method for producing antigen-comprising microparticles according to any one of [18] to [20]; and
preparing a pharmaceutical composition by incorporating the antigen-comprising microparticles and a pharmaceutically acceptable carrier.

Advantageous Effect of the Invention

The present invention provides a bioactive peptide which includes a partial amino acid sequence of *Plasmodium falciparum* enolase, and which has a molecular structure compatible with the specification setting for a GMP-compliant production process. In particular, this peptide has characteristics that the confirmation test (mass spectrometry analysis, HPLC analysis) of the drug substance can be carried out easily. The peptide according to the present invention can be used as a material for diagnosing *falciparum* malaria infection, by allowing the peptide to react with the serum of a patient, and as an antigen for immunization capable of inducing the production of antibodies which inhibit the proliferation of *Plasmodium falciparum*. In other words, the peptide according to the present invention can be used: as a symptom-improving agent which induces active immunity, for patients with *falciparum* infection; and as a vaccine which induces protective immunity, for non-infected individuals.

BRIEF DESCRIPTION OF THE DRAWINGS

In FIG. 8, absorbance in ELISA at a dilution of 250-fold was used, and values obtained by subtracting the absorbance value at week 0 from the absorbance values at respective weeks were plotted to prepare the graph.

In FIG. 9, the absorbance in ELISA at a dilution of 250-fold was used, and values obtained by subtracting the absorbance value at week 0 from the absorbance values at respective weeks were plotted to prepare the graph.

FIG. 10 shows a comparison of amino acid sequences between *P. falciparum* enolase (GenBank accession number: AB026051) (SEQ ID NO: 3) and Human alpha enolase, GenBank accession number: M14328) (SEQ ID NO: 4). AD22 is indicated with an underline, and AT28 is indicated with an underline and a dashed line.

FIG. 14 shows partial sequence structures of hitherto reported enolase molecules, illustrating the portions thereof involved in the binding of plasminogen. A partial peptide of *P. falciparum* (SEQ II) NO: 18), a partial peptide of *Streptococcus pneumoniae* enolase (SEQ ID NO: 19), and a partial peptide of Human α enolase (SEQ ID NO: 20).

DESCRIPTION OF THE EMBODIMENTS

Figure 1:
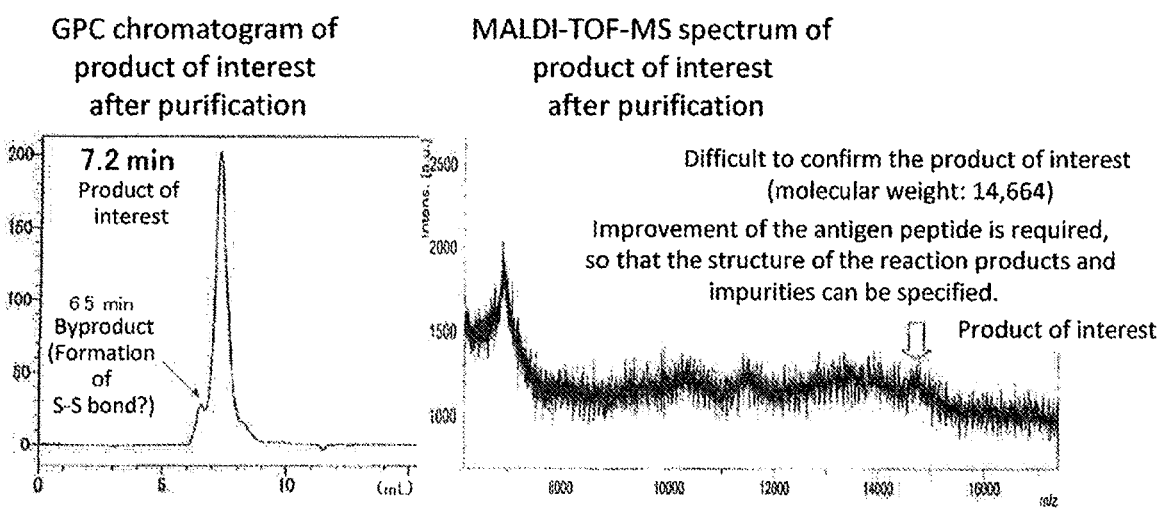
FIG. 1 shows the analysis results (a GPC chromatogram and a MALDI-TOF-MS spectrum) of an antigen peptide represented by Formula (A) obtained by a conventional method.

The present invention will now be described in detail.

The present invention relates to the following peptide prepared based on a partial sequence of a protein derived from a malaria parasite.

A peptide having a structure in which two peptides each having (i) an amino acid sequence represented by: A01-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-A02 (SEQ ID NO: 1) or (ii) an amino acid sequence represented by: A03-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Lys-Ser-Leu-Val-Lys-Thr-A04 (SEQ ID NO: 2) are linked by amide bonds between the respective carboxy termini of the two peptides and two amino groups of Lys in a linker peptide represented by the following (iii):

(iii) Lys-A05-Cys-A06 and arranged in the form of a two-forked branch (wherein in the above (i), (ii), and (iii), A01 to A06 each represents an amino acid residue(s) in a number of an arbitrary number including 0).

The peptide shown in the Sequence Listing as SEQ ID NO: 1 is a peptide in which the numbers of amino acid residues in A01 and A02 in the sequence of (i) are both 0.

The peptide shown in the Sequence Listing as SEQ ID NO: 2 is a peptide in which the numbers of amino acid residues in A03 and A04 in the sequence of (ii) are both 0.

Each of A01 and A03 preferably consists of 0 to 10 amino acid residues, and the sequence thereof is not particularly limited as long as it does not affect the immune responsiveness of the resulting antigen peptide. However, it is more preferred that each of the A01 and A03 consist of 3 to 10 consecutive acidic amino acid residues (glutamic acid or aspartic acid) or basic amino acid residues (lysine, arginine or histidine), in order to increase the solubility of the entire peptide.

Each of A02 and A04 preferably consists of 0 to 10 amino acid residues, more preferably 1 to 5 amino acid residues, and the sequence thereof is not particularly limited as long as it does not affect the immune responsiveness of the resulting antigen peptide. However, each of A02 and A04 preferably has a sequence which allows for securing the degree of freedom of binding between each enolase peptide and the linker. Each of A02 and A04 may be, for example, Pro-Yaa or Lys-Yaa (Yaa is an amino acid residue having a high degree of freedom, such as Gly or Pro) Alternatively, each of A02 and A04 may be Pro-Yaa-Cys or Lys-Yaa-Cys.

A05 preferably consists of 0 to 10 amino acid residues, and the sequence thereof is not particularly limited as long as it does not affect the immune responsiveness of the resulting antigen peptide. However, it is more preferred that A05 consist of 3 to 10 consecutive acidic amino acid residues or basic amino acid residues, in order to increase the solubility of the resulting peptide.

A06 preferably consists of 0 to 10 amino acid residues and the sequence thereof is not particularly limited as long as it does not affect the immune responsiveness of the resulting antigen peptide. However, in the case of carrying out solid-phase synthesis on a resin, A06 preferably consists of amino acid residues including βA (β-alanine) at its carboxy terminus, as the first amino acid with a low steric hindrance. Alternatively, A06 may consist of βA. However, it can be substituted by another residue as long as the peptide synthesis reaction is not interfered with. Further, a modifying group for improving lipophilicity, such as palmitoyl group, may be added to a portion of amino acids constituting A06. For example, A06 may be Lys-βA. in which a modifying group is added to the side chain amino group of Lys. Addition of a lipophilic modified group is advantageous, because it is possible to expect an improvement in compatibility with a non-ionic surfactant (such as Tween or Span) used in the formulation of pharmaceuticals, or an improvement in antigenicity due to self-assembly. Instead of palmitoyl group, a highly lipophilic carboxylic acid can be bound by an amide bond, to serve as a suitable modifying group. Examples of such carboxylic acids include stearic acid, myristic acid, lauric acid, oleic acid, linoleic acid, cholic acid, and the like.

Examples of preferred embodiments of the peptide according to the present invention include a peptide represented by the following (I) or (II):

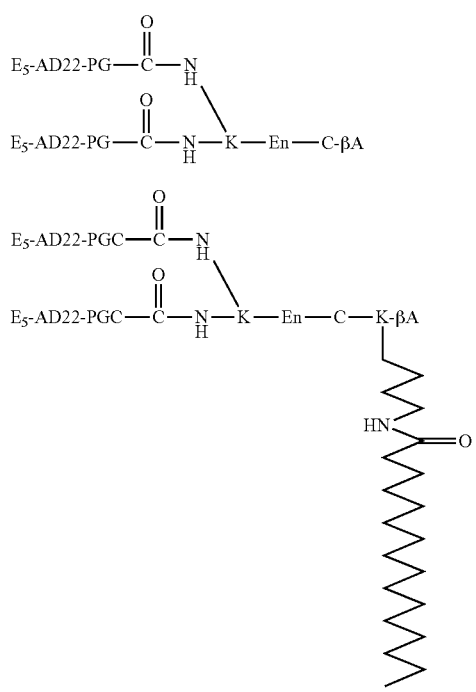

In the above (I) and (II), $E_5$ represents a sequence of five consecutive Glu residues, and AD22 represents the amino acid sequence of SEQ ID NO: 1. PG represents a Pro-Gly sequence, and G represents the portion of a Gly residue excluding the carboxyl group. Further, K at the branching site represents the portion of a Lys residue excluding two amino groups, and an $E_5$-AD22-PG- sequence or an $E_5$-AD22-PGC-sequence is bound to each of the two amino groups of the Lys residue. En represents a sequence of four or five consecutive Glu residues. En is preferably $E_4$, which is a sequence of four consecutive Glu residues, namely, En *herein n is 4. C represents a Cys residue. The C terminus represents a βAla residue, or a sequence of a Lys residue whose side chain amino group is palmitoylated and a βAla residue. The N terminus is a non-protected amino group, and the C terminus is a non-protected carboxyl group, but each may have a protected group.

A more preferred embodiment of the present invention is a peptide having a dimerized structure in which two peptides described above are linked by an S—S bond between the Cys residues in the linker peptide sequences, each represented by the above (iii), included in the respective two peptides. In other words, it is preferred that the peptide represented by (i) or (ii) be dimerized by a peptide represented by (iii), and, the two of the dimerized peptides are further linked by an S—S bond between the Cys residues, to have a tetramerized structure.

Specific examples thereof include the following two types of peptide structures.

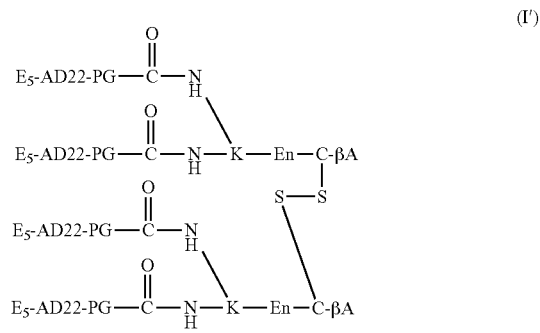

In the above (I'), $E_5$ represents a sequence of five consecutive Glu residues, and AD22 represents the amino acid sequence of SEQ ID NO: 1. PG represents a Pro-Gly sequence, and G represents the portion of a Gly residue excluding the carboxyl group. Further, K at the branching site represents the portion of a Lys residue excluding two amino groups, and an $E_5$-AD22-PG-sequence is bound to each of the two amino groups of the Lys residue. En represents a sequence of four or five consecutive Glu residues. En is preferably $E_4$, which is a sequence of four consecutive Glu residues, namely, En wherein n is 4. C represents the portion of a Cys residue excluding the mercapto group, and a state is shown in which a disulfide bond (—S—S—) is formed between the side chains of the two Cs. βA at the C terminus represents a βAla residue. The N terminus is a non-protected amino group, and the C terminus is a non-protected carboxyl group, but each may have a protected group.

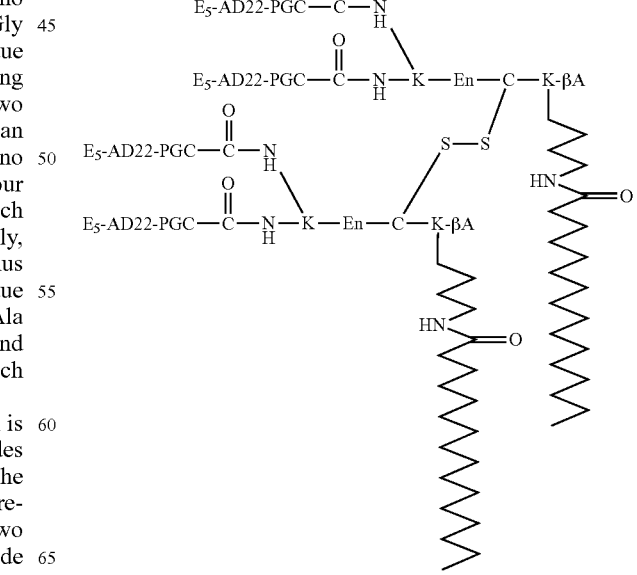

In the above (II'), $E_5$ represents a sequence of five consecutive Glu residues, and AD22 represents the amino acid sequence of SEQ ID NO: 1. PGC represents a Pro-Gly-Cys sequence, and C represents the portion of a Cys residue excluding the carboxyl group. Further, K at the branching site represents the portion of a Lys residue excluding two amino groups, and an $E_5$-AD22-PGC- sequence is bound to each of the two amino groups of the Lys residue. En represents a sequence of four or five consecutive Glu residues. En is preferably $E_4$, which is a sequence of four consecutive Glu residues, namely, En wherein n is 4. C represents the portion of a Cys residue excluding the mercapto group, and a state is shown in which a disulfide bond (—S—S—) is formed between the side chains of the two Cs. —K—βA at the C terminus side represents a sequence of a Lys residue whose side chain amino group is palmitoylated and a βAla residue. The N terminus is a non-protected amino group, and the C terminus is a non-protected carboxyl group, but each may have a protected group.

These peptide structures can be produced based on a general method for synthesizing a peptide. More specifically, the peptide structures can be produced by a method described in Examples to be described later.

The present invention also provides microparticles containing any of the above described peptides, and a method for producing the same. The particle diameter of the microparticles is not particularly limited, and it can be adjusted depending on the application. However, the microparticles preferably have a particle diameter of from 100 nm to 50 μm.

The microparticles may be, for example, microparticles containing a bioactive substance and a biodegradable polymer, as those disclosed in JP 2009-256324 A, wherein the microparticles are prepared by: a step of mixing a volatile organic acid aqueous solution containing the bioactive substance or a volatile organic acid solution of the bioactive substance with a volatile organic solvent containing the biodegradable polymer to prepare an emulsion; and a step of mixing the resulting emulsion with an aqueous solution of a negatively-charged polymer. The biodegradable polymer to be used in the production of the microparticles is preferably a polylactic acid-glycolic acid copolymer or a polydepsipeptide. The volatile organic acid can be selected from organic compounds including a carboxylic acid group, which are liquid at normal temperature. Examples thereof include acetic acid and formic acid. Other examples include: compounds which include a hydroxyl group as a functional group other than a carboxylic acid group, such as lactic acid; and compounds which include a plurality of carboxylic acid groups, such as fumaric acid, malonic acid, and malic acid; and the like. As the volatile organic solvent, an organic solvent which is volatile, which does not mix well with water, and which is capable of dissolving a biodegradable polymer is used. Preferred examples thereof include dichloromethane, chloroform, ethyl acetate, diethyl ether, and the like. The negatively-charged polymer may be, for example, a polymer containing an oxygen atom. Preferred examples thereof include polyvinyl alcohol, carboxymethyl cellulose, and polyethylene glycol. An example of the microparticles produced by the above mentioned production method is: a W/O/W-type emulsion or dried microparticles of the emulsion, whose outermost layer contains the negatively-charged polymer, Whose middle layer contains the biodegradable polymer, and whose inner layer contains the peptide according to the present invention; or alternatively, a W/O-type emulsion or dried microparticles of the emulsion, whose outer layer contains the negatively-charged polymer, and whose inner layer contains the biodegradable polymer and the peptide according to the present invention.

Further, the microparticles may be, for example, microparticles which allow the presentation of the peptide on the surface of the polymer, such as those disclosed in JP 2012-240940A.

The antigen peptide according to the present invention and the microparticles containing the antigen peptide may be used along with an adjuvant containing aluminum ions. Aluminum hydroxide gel (alum), which is a commonly used adjuvant, can be uniformly suspended with microparticles, and an effect provided by the adjuvant further enhances the antigenicity of the antigen peptide. For example, the selection of an optimal aluminum salt or the design of the microparticles can be performed, referring to Lindblad, Vaccine, 2004, Vol. 22, page 3658 to 3668, and references cited therein.

In addition, an adjuvant other than aluminum ions may be used in the present invention. The adjuvant may be incorporated into microparticles along with the antigen, or may be incorporated into saline. Incorporation of the adjuvant further enhances the antigenicity of the antigen peptide. For example, the selection of an optimum adjuvant or the design of the microparticles can be performed, referring to Guy, Nature Reviews Microbiology, 2007, Vol. 5, page 505 to 517, and reference cited therein.

Further, the antigen peptide according to the present invention and the microparticles containing the antigen peptide may be combined with a pharmaceutically acceptable carrier, to form a pharmaceutical composition. The carrier may be incorporated into the microparticles along with the antigen, or may be incorporated into saline. Examples of the pharmaceutically acceptable carrier include components which are acceptable in the formulation process, such as buffers, freeze-drying auxiliary agents, stabilizing auxiliary agents, solubilizing auxiliary agents, and antibacterial agents. Examples of the buffer include phosphate, citrate, sulfo sulfosalicylate, acetate, and the like. Examples of the freeze-drying auxiliary agent include mannitol, lactose, sorbitol, dextran, Ficoll, polyvinylpyrrolidin (PVP), and the like. Examples of the stabilizing auxiliary agent include ascorbic acid, cysteine, monothioglycerol, sodium hydrogen sulfite, sodium metabisulphite, gentisic acid, inositol, and the like. Examples of the solubilizing auxiliary agent include ethanol, glycerin, polyoxyethylene sorbitan monooleate, sorbitan monooleate, polysorbates, poly(oxyethylene) poly(oxypropylene) poly(oxyethylene) block copolymers (Pluronics), lecithin, and the like. Examples of the antibacterial agent include benzyl alcohol, benzalkonium chloride, chlorbutanol, methylparaben, propylparaben, butylparaben, and the like.

The dosage form of the pharmaceutical composition is not particularly limited, and examples thereof include injectable solutions, oral preparations, liniments, and the like. Of these, an injectable solution is preferred. The injectable solution can be prepared by dissolving the microparticles in a diluent or the like, and adding to the resultant a stabilizer, a preservative, a buffer, and/or the like, as necessary.

A subject to be administered is a mammal infected with malaria, or a mammal having a risk of being infected or suspected to be infected with malaria. Specific examples thereof include humans, monkeys, mice, rats, and the like. The subject is preferably a human.

Examples of malaria include: malaria caused by a single infection with *falciparum* malaria parasite (*P. falciparum*);

malaria caused by an infection with a human or simian malaria parasite; and malaria caused by a mixed infection with these parasites.

The dose of the pharmaceutical composition according to the present invention to a human varies depending on the age, sex, body weight and immune status of a subject, the method of administration, or the proportion of a bioactive substance contained in the pharmaceutical composition. However, the dosage is preferably from 1 µg to 200 mg per single administration.

The number of doses is not limited. When administered multiple times with regular intervals therebetween, an increase in and maintenance of antibody titer can be expected due to a boosting effect. The "regular interval" is preferably a period of time from two weeks to six months, and more preferably from three weeks to three months. The "multiple times" is preferably from two to 20 times, and more preferably from two to four times.

The method of administration is not particularly limited. Examples thereof include a method in which the antigen peptide, antigen peptide-containing microparticles, or a pharmaceutical composition in the form of microparticles containing the antigen peptide, is/are suspended, in saline, and the resultant is administered to a subject by an intramuscular injection, a subcutaneous injection or an intradermal injection to the upper arm of a subject. It is expected that this administration method allows the microparticles to penetrate into muscular tissue or the intradermal or subcutaneous portion of the site of administration, and the antigen peptide or a pharmaceutical preparation thereof is then taken up by immune cells, eventually inducing humoral immunity or cell-mediated immunity. This method has been conventionally used, and will probably continue to be widely used, because of its reliability.

Examples of the administration method other than the above include a method in which the suspension in saline is administered to the nasal cavity. The method of administration to the nasal cavity may be, for example, a method using a spray or a syringe, but not limited thereto. It is thought that the method of administration to the nasal cavity allows the antigen peptide to penetrate into the nasal mucosa, and the antigen peptide is then taken up by immune cells, eventually inducing humoral immunity or cell-mediated immunity. This nasal administration method is considered to be better in terms of safety, as compared to the method by a subcutaneous injection. Further, the nasal administration differs from the subcutaneous administration in that it is expected, in general, to induce a higher production of secretory IgA antibody in the mucous membrane. Accordingly, the nasal administration is considered as a suitable method for complementing the subcutaneous administration method, in the treatment of a parasitic infection, such as malaria, caused by parasites which proliferate in red blood cells.

Further, the administration method other than those described above, may be, for example, a subcutaneous or intradermal administration method using a dosage form referred to as a patch or a poultice, which is applied topically on the skin of the upper arm. It is expected that these administration methods allow the antigen peptide to penetrate into the intradermal or subcutaneous portion of the site of administration, and the antigen peptide is then taken up by immune cells, eventually inducing humoral immunity or cell-mediated immunity. These methods are considered to be better in terms of safety, as compared to the method by a subcutaneous injection. On the other hand, there remains a practical problem that whether all the antigen peptide in the pharmaceutical preparation is able to penetrate into the intradermal or subcutaneous portion of the administration site, as compared to the case of subcutaneous injection.

The bioactive peptide according to the present invention or a pharmaceutical composition containing the same can be used as an antigen for inducing an immune response, namely, as a vaccine. This allows for preventing an infection with or the development of malaria, improving the immunity of a patient to inhibit the progression of symptoms, or ameliorating the symptoms.

In the present invention, the term "immune response" is a concept which encompasses both a cell-mediated immune response and a humoral immune response. Of these, the cell-mediated immune response refers to an immune response induced, for example, by macrophages, natural killer cells (NK cells), eosinophils, and T-cells. As the cell-mediated immune response against *P. falciparum*, an immune response in which killer T-cells are involved is known. As the humoral immune response, an immune response induced by host-derived antibodies capable of specifically binding to a protein or a sugar chain derived from *P. falciparum* is known. It is desirable that the antigen peptide produced according to the present invention induce antibodies, as the humoral immune response. Further, the immune response induced by the antigen peptide according to the present invention is preferably an immune response which blocks or inhibits the interaction between enolase and plasminogen, which interaction is caused by malaria infection.

The bioactive peptide according to the present invention can be used as a diagnostic testing material for diagnosis and testing of malaria, by allowing the bioactive peptide to bind to, immobilized on, or adsorbed on, a solid phase surface. In other words, as one embodiment of the present invention, it is possible to provide a substance for examination and diagnosis of malaria, which substance is obtained by allowing the peptide according to the present invention to bind to a solid phase surface. Examples of the solid phase surface include a film, latex particles, a plastic plate, microbeads, and the like, but not limited thereto. For example, the peptide compound according to the present invention in the form of a film can be prepared by a spin casting method, and it is possible to detect the presence of antibodies in a test sample by dropping the test sample on the film. The compound according to the present invention bound to latex particles can be prepared according to an emulsion polymerization method or a suspension polymerization method, and the compound can be used in an agglutination reaction. The immobilization of the peptide on a plastic plate or microbeads can be carried out, for example, by dropping an adequate amount of the compound according to the present invention adjusted to a concentration of 50 µg/0.1 mL into wells of the plastic plate, or by immersing the microbeads in the solution of the present invention adjusted to a concentration of 200 µg/0.1 mL. The laboratory diagnosis materials as described above are expected to be used in: the test for measuring malaria antibody titer in serum or plasma; the analysis of the immune response to the antigen peptide of the present invention; and the measurement of the antibody titer in an individual immunized with the antigen peptide of the present invention.

A summary will now be given below regarding: a pharmaceutical preparation which is used by suspending the bioactive peptide-containing microparticles or the pharmaceutical composition in the form of microparticles containing the bioactive peptide, in saline; and a kit of the pharmaceutical preparation; with reference to an example expected when applied to a human, in particular. However, the summary, the composition, and the properties of pharmaceutical preparations which are conceivable based on the present invention are not limited thereto.

For example, according to the method disclosed in JP 2009-256324 A, the microparticles can be prepared with an antigen content (weight of antigen/ weight of microparticles) of from about 0.1 µg/mg to 100 µg/mg. Practically, the antigen content is preferably within the range of from 1 µg/mg to 50 µg/mg, and more preferably within the range of from 1 µg/mg to 30 µg/mg, in terms of achieving a persistent antibody titer, and of preparing ideal microparticles capable of releasing antigen at a constant rate (zero-order release).

In general, one kit (2.0 mg of microparticles and 0.5 mL of saline) corresponds to a dose per administration for an adult. In general, the upper limit of the dose of an antigen is determined by a safety test using a rodent or a non-rodent. However, since the present preparation includes a peptide antigen having a relatively high safety, it is expected that the dose of the antigen per administration can be set within a wide range of from 1 µg to 200 µg. Practically, in terms of antibody titer persistence and production cost, the dose of the antigen per administration is preferably from 2 µg to 100 µ, and more preferably from 4 µg to 60 µg.

Further, the kit may be a pharmaceutical preparation kit consisting of two vials or ampoules separately containing microparticles and saline, or a kit consisting of an all-in-one pre-filled syringe, for the purpose of securing safety upon administration and/or avoiding the use of a preservative (such as thimerosal), but not limited thereto.

[Summary Example of Pharmaceutical Preparation and Pharmaceutical Preparation Kit]

(a) Summary of Pharmaceutical Preparation

The present preparation includes as an antigen a 22-residue partial sequence of a glycolytic enzyme, enolase, derived from *P. falciparum*, which has been reported as an antigen involved in the convalescent phase of malaria, based on the epidemiological surveys in malaria endemic areas and in Japan. Further, the present preparation utilizes an intelligent material, which allows for a sustained release of the antigen from PLGA (polylactic acid-glycolic acid copolymer) microparticles. This is based on an idea of reproducing an immune status similar to that of the residents in endemic area, who generally maintain immunity to malaria due to persistent infection. The antigen is encapsulated in microspheres of PLGA (polylactic acid-glycolic acid copolymer).

The antigen is a chemically synthesized peptide antigen having a tandem structure in which four 22-residue peptides (AD22) are tandemly arranged, and has a structure represented by the above described Structural Formula (I'). The present preparation is used as a liquid preparation prepared by suspending the microparticles in saline upon use. The antigen has been analyzed by a high performance liquid chromatograph and an amino acid analyzer during the production process, and confirmed to be the antigen having a structure represented by the Structural Formula (I').

(b) Composition

One kit (5.0 mg of microparticles and 0.5 mL of saline) of the present preparation includes the following components.

Effective ingredient: AD22 synthetic peptide antigen (I'): 50 µg.

Additives: The microparticles are mostly composed of a polylactic acid-glycolic acid copolymer (about 5.0 mg) and contain a trace amount of polyvinyl alcohol which is coated on the surface of the particles. In addition, 4.25 mg of sodium chloride is contained in 0.50 mL of saline, so that the microparticles can be suspended in the saline.

(c) Properties of Microparticles

Appearance and properties: Colorless and odorless micro powder.

Solubility: Easily dispersed in saline or purified water (usually used at a concentration of from 1 to 10 mg/0.1 mL).

Hygroscopicity: Have no deliquescence due to the outer surface being coated by polyvinyl alcohol.

Melting point and others: Soften at about 60° C. or higher due to being composed of a polymeric material.

Other characteristic values: Observed by an electron microscope to be spherical microparticles having a particle size of from 0.1 to 40 µm.

Quantification method of effective ingredient: The antigen content in the microparticles (weight of antigen/ weight of microparticles) is quantified from the CHN composition ratio obtained by a solvent extraction method (methylene chloride-aqueous solvent) or elemental analysis (the content in the present preparation is 10±1 µg/mg).

(d) Properties During Use

The present preparation is used as a liquid preparation prepared by suspending 5 mg of the microparticles in 0.5 mL of saline upon use. When the microparticles are suspended in saline and mixed by shaking, the resulting liquid preparation becomes uniformly clouded.

pH: 5.5 to 8.0

Ratio of osmotic pressure (ratio with respect to saline solution): approximately 1

Next, an example in the case of administration to humans will be described below. However, the dose, the interval(s) between doses, and the number of doses are not limited thereto.

[Potency or Effect]

(e) Potency or Effect/Usage and Dose

Prevention of aggravation of malaria infection: In general, a dose of 0.5 mL of the present preparation is injected subcutaneously or intramuscularly, twice at an interval of four weeks, followed by another injection of 0.5 mL after the passage of 20 to 24 weeks. However, to an individual under 10 years old, a dose of 0.25 mL is injected subcutaneously, at the same dose intervals.

However, in cases where an inoculated subject failed to acquire active AD22 antibody, an additional injection(s) is/are administered.

**Note that an antibody test is to be carried out about one to two months after the third inoculation of the present preparation, and an additional inoculation(s) is/are to be considered to an inoculated subject who has failed to acquire AD22 antibody.

(f) Efficacy

Prevention of aggravation of malaria infection: AD22 antigen, *P. falciparum*-derived enolase When adults and children negative for AD22 antibody are inoculated with 0.5 mL (0.25 mL, for those under 10 years old) of the present preparation three times, it is expected that most of the inoculated subjects become positive for AD22 antibody. Further, in the case of individuals infected with malaria in malaria endemic areas, it is expected to be able to delay the aggravation of the symptoms, and to prevent death due to delay in the start of treatment.

(g) Safety

Based on common cases, side reactions are expected in about 10% of the inoculated subjects. Primary side reactions expected include: topical pain, swelling, feeling of heat, feeling of fatigue, headache or dull headache, fever, and the like. It is considered that the present preparation is less likely to cause induration, which is often seen with the use of an alum adjuvant often used in a pre-existing vaccine, due to difference in components.

(h) Pharmacology

When malaria parasites enter the body of an individual who had been bitten by a mosquito that transmits malaria parasites, the parasites swiftly migrate into the liver cells. After a certain incubation period in the liver cells, the parasites proliferate in the liver cells, and are released into the blood stream in one of the forms of the parasites, called merozoites, and then invade red blood cells. The merozoites proliferate in the red blood cells, and are then released into the blood stream again as merozoites, and invade the red blood cells again. In this manner, the merozoites keep proliferating. The symptom of fever due to infection with malaria is induced by the intraerythrocytic cycle. In the case of an infection with *Plasmodium falciparum*, there is a higher risk of developing severe symptoms and of death when the start of treatment is delayed, as compared to malaria caused by other three species of malaria parasites. Infants and toddlers in endemic areas and travelers from non-endemic areas who do not have immunity are known to be particularly at a high risk of developing severe symptoms.

However, when the merozoites invade red blood cells, antibodies are also taken into the cells, at the same time. The antibodies taken up into the red blood cells prevent or inhibit the proliferation of the parasites, by blocking the enzyme reaction of enolase in the glycolytic pathway which produces the energy required for the proliferation of the parasites. At the same time, since enolase is known to be localized on the surface of a merozoite, it also seems probable that the antibodies react with the epitopes of enolase, thereby preventing or inhibiting the invasion of the parasites into red blood cells. These mechanisms of action as described above allow for delaying the aggravation of the symptoms when infected with malaria, and for preventing death due to delay in the start of treatment.

EXAMPLES

The present invention will now be further described in detail, with reference to Examples. However, the present invention is in no way limited to these Examples, as long as the gist of the present invention is not deviated.

Role of enolase and plasminogen in malaria parasite infection:

In recent years, it has been reported that the binding between plasminogen in human blood and enolase on the surface of the parasites facilitates the invasion of malaria parasite into a host [Ghosh A K, Coppens I, Gardsvoll H, Ploug M, Jacobs-Lorena M. *Plasmodium ookinetes* coopt mammalian plasminogen to invade the mosquito midgut. Proc Natl Acad Sci U S A. 2011, vol. 108, pp. 17153-17158; Bergmann S, Wild D, Diekmann O, Frank R, Bracht D, Chhatwal G S, Hammersclunidt S. Identification of a novel plasmin(ogen)-binding motif in surface displayed alpha-enolase of *Streptococcus pneumoniae*. Mol Microbiol. 49(2): 411-423, 003. ; Ghosh A K, Jacobs-Lorena M. Surface-expressed enolases of *Plasmodium* and other pathogens. Mem Inst Oswaldo Cruz. 106(Suppl 1): 85-90, 2011.]. In other words, plasmin activity on the parasite surface, namely, proteolytic activity, is assumed to facilitate the invasion of parasites into host cells. However, cases reported in detail are only those in which the invasion of parasite ookinetes into the mid-gut of a mosquito is confirmed, and other expected cases of invasion, such as invasion into liver cells and red blood cells, have not been directly confirmed.

As described above, the present inventors have discovered that the molecule of *P. falciparum*-derived enolase strongly reacts with the serum of a patient having a certain immunity to *falciparum* malaria, based on epidemiological surveys, arid thus studied *P. falciparum*-derived enolase as a vaccine candidate. At first, the inventors assumed that IgG antibody would inhibit the action of an enzyme functioning in the energy production system in cells. Therefore, when IgG failed to migrate into cells, there was no valid explanation to account for the contradiction. In other words, it was unable to explain how the high anti-enolase antibody titer, which has been epidemiologically observed in residents in malaria endemic areas, is contributing to a reduction in the percentage of parasitism of malaria parasites.

Although, it was already known that enolase is expressed on the surface of merozoites, at the initial stage of the study [Kano S, Nakamura N, Murakami T, Ishikawa H, Suzuki M. Localization of 47 kD antigenic polypeptides in malaria parasites by confocal laser scanning microscopy. Bioimages. 3(1): 13-17, 1995.], it was unable to explain, at that time, that why a glycolytic enzyme is observed on the parasite surface. Years of studies have finally led the present inventors to an idea that the high anti-enolase antibody titer, which has been epidemiologically observed in the residents in malaria endemic areas, may be responsible for inhibiting the binding between enolase on the surface of merozoite parasites and human plasminogen (and further, inhibiting the invasion of ookinetes and merozoites into host cells).

Plasminogen Binding Sites in Malaria Parasite Enolase:

Plasminogen is usually contained in plasma, and is activated by binding to a receptor protein. Plasminogen is a protein consisting of 791 residues, and one plasminogen includes five kringle domains and a serine protease domain. The kringle domain is composed of about 80 amino acids, and has a distinctive secondary structure including three sets of S—S crosslinking. It has been reported that, the binding of the receptor protein to the kringle domain causes the hydrolysis of the plasminogen activator site, to allow the development of plasmin activity, thereby facilitating the invasion of ookinetes into the mid-gut of a mosquito. [Ghosh A K, Coppens I, Gardsvoll H, Ploug M, Jacobs-Lorena M. *Plasmodium ookinetes* coopt mammalian plasminogen to invade the mosquito midgut. Proc Natl Acad Sci U S A. 2011, vol. 108, pp. 17153-17158.; Bergmann S, Wild D, Diekmann O, Frank R, Bracht D, Chhatwal G S, Hammerschmidt S. Identification of a novel plasmin(ogen)-binding motif in surface displayed alpha-enolase of *Streptococcus pneumoniae*. Mol. Microbiol. 2003, 49, 411-423.; Ghosh A K, Jacobs-Lorena M. Surface-expressed enolases of *Plasmodium* and other pathogens. Mem Inst Oswaldo Cruz. 2011, 106(Suppl 1), 85-90.]

Based on the comparison of the reported sequences of enolase in other pathogenic microorganisms, the plasminogen binding sites in enolase are estimated to be, when converted into the amino acid sequence of malaria parasites, within the region of approximately from 260th to 285th amino acids. Surprisingly, the above region corresponds well with the AD22 sequence (Ala256-Asp277) and AT28 sequence (Ala256-Thr283) of the peptide antigen, whose reactivity with the serum of patients has been investigated by the present inventors [Nonaka R, Oku H., Sato K, Kano S., Suzuki M, Katakai R. Synthesis of Small Domain Peptides of Glycolytic Enzyme Enolase, Peptide Science 2000, T. Shioiri, Ed.; Protein Research Foundation: Osaka; pp. 301-304 (2001).].

As described above, the prior art was unable to account for the mechanism by which the high anti-enolase antibody titer, which has been epidemiologically observed in the residents in malaria endemic areas, contributes to a reduction in the percentage of parasitism of malaria parasites. However, the combination of recently reported cases and the study of the present inventors finally led to an idea that the anti-enolase antibody may be responsible for inhibiting the binding between enolase on the surface of merozoite parasites and human plasminogen (and further, the invasion of ookinetes and merozoites into host cells). Therefore, the inventors carried out an experiment to confirm the presence or absence of plasminogen binding sites in the antigen sequence they have been studying.

Reference Example 1

Figure 2:
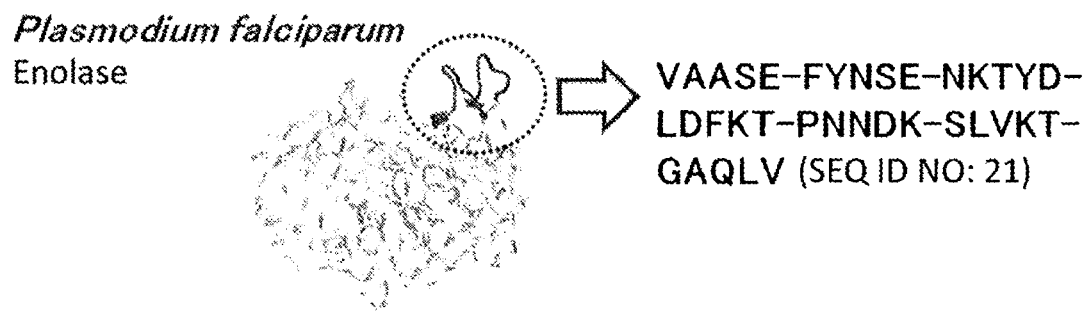
FIG. 2 is a diagram showing the molecular structure of *Plasmodium falciparum* enolase, and a loop structure (the portion surrounded by the dotted in which a 35-residue sequence (amino acid numbers 254 to 288 in SEQ ID NO: 3: SEQ ID NO: 21) is located.
Figure 11:
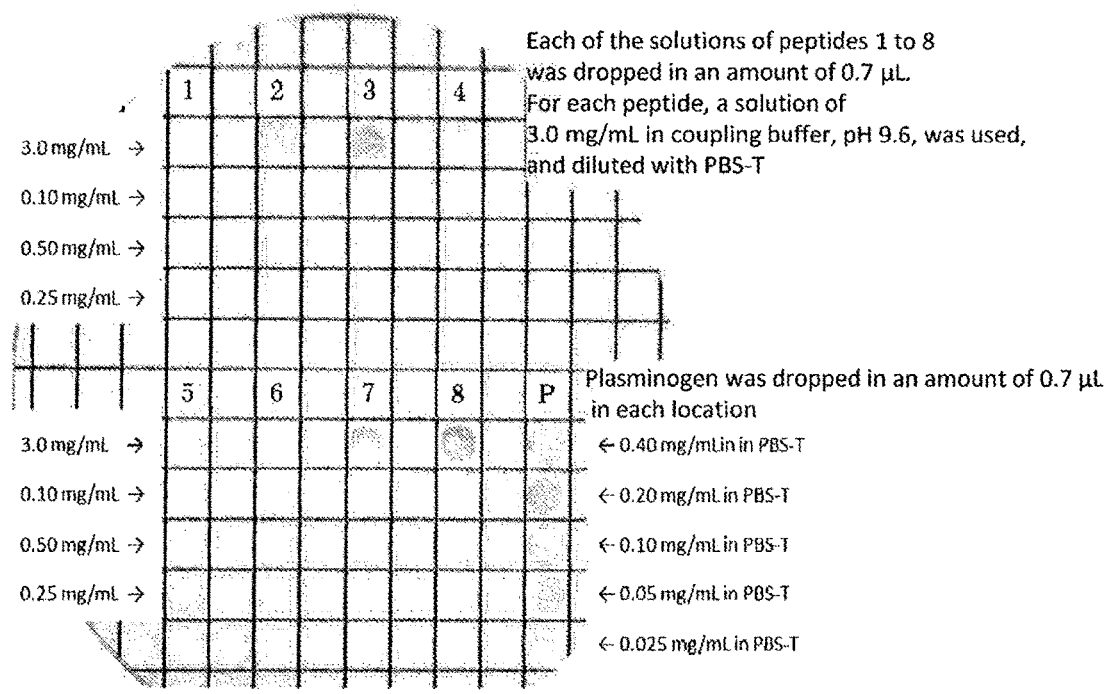
FIG. 11 is a photograph after staining with DAB reagent in a Dot-Blot measurement, for detecting the binding between each of the peptide 1 to peptide 8 and plasminogen. The numbers 1 to 8 in FIG. 11 indicate the locations at which peptide solutions of the peptide 1 to peptide 8 were dropped, respectively, and P indicates the locations at which plasminogen solutions (positive control) were dropped.
Figure 12:
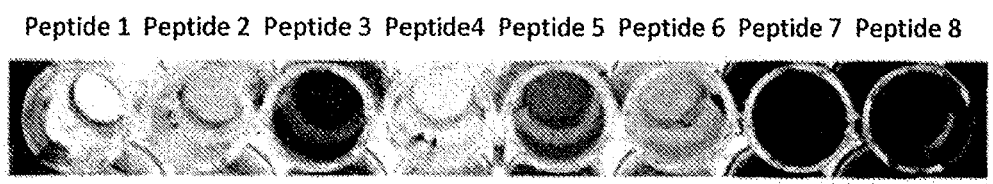
FIG. 12 is a photograph of a plate after staining with TMB reagent in an ELISA measurement, for detecting the binding between each of the peptide 1 to peptide 8 and plasminogen. Each of the peptide 1 to peptide 8 was immobilized in each of the wells of the plate, and then allowed to react with plasminogen. Detection of binding was carried out by staining with an HRP modified-anti-plasminogen antibody and TMB reagent.
Figure 13:
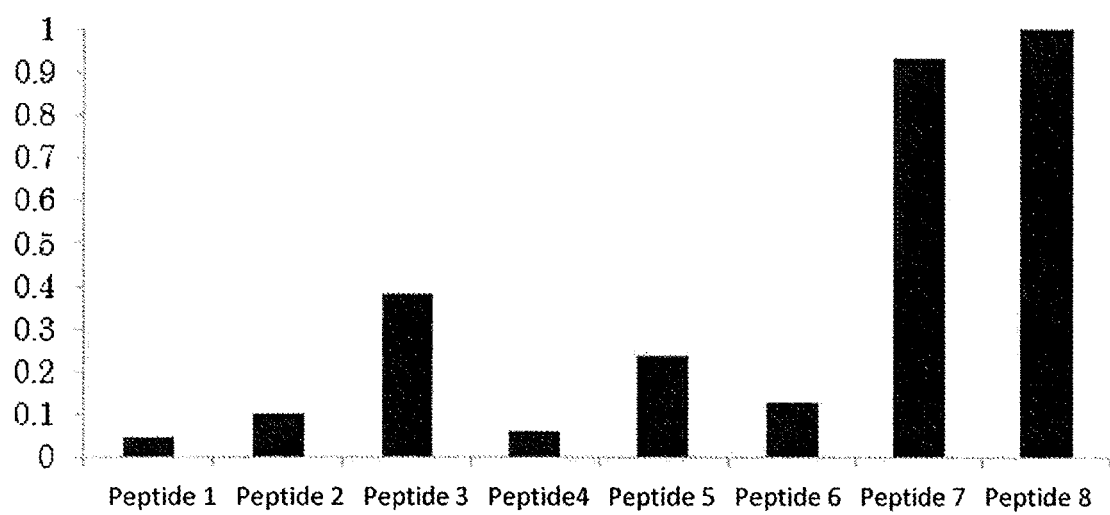
FIG. 13 is a graph of absorbance data (at 450 nm) taken after staining with TMB in an ELISA measurement, for detecting the binding between each of the peptide 1 to peptide 8 and plasminogen (plasminogen concentration: 1 μg/well).

A peptide library of peptides 1 to 8 (SEQ ID NOs: 10 to 17), which are divided peptides obtained from a 35-residue sequence of 254th to 288th residues (FIG. 2) of the amino acid sequence of the parasite enolase, was used. Each of the peptides of the peptide library was allowed to react with plasminogen using a Dot-Blot method and an ELISA method, thereby carrying out a search for an amino acid sequence recognized by plasminogen.
Reactivity of Peptide Library with Plasminogen, Measured by Dot-Blot Method:

The reactivity of the peptides was measured by a Dot-Blot method, using a 10% acetonitrile solution of each of 8 types of peptides, peptide 1 to peptide 8, by the following steps in the following order; (a) immobilization of each peptide on a nitrocellulose film (pore size: 0.45 μm); (b) reaction with plasminogen in a plasminogen solution; (c) reaction with an HRP-labeled anti-plasminogen antibody; and (d) DAB staining. The photograph of the nitrocellulose film after the DAB staining is shown in FIGS. 11 and 12. As a result of the measurement, the binding of peptide chains with plasminogen was observed in the peptides 2, 3, 7 and 8.
Reactivity of Peptide Library with Plasminogen, Measured by ELISA Method:

Next, in order to digitize and quantify the reaction of the peptide library with plasminogen, the detection of binding by an ELISA method was carried out. The results are shown in FIG. 13. It can be seen from the measurement result that a relatively high reactivity with plasminogen was observed in the peptides 3 and 5, which are 10-residue peptide sequences. Further, a high reactivity with plasminogen was observed in the peptide 7 which is a 25-residue peptide sequence, and in the peptide 8 which is a 35-residue peptide sequence. It was found out that, among the 10-residue peptides in the library, the highest reactivity with plasminogen was observed in the peptide 3.
Discussion on Data Obtained by Dot-Blot and ELISA Methods:

The ELISA measurement revealed that the peptide 3 has the highest reactivity with plasminogen, among the 10-residue peptides in the library. When the sequence of the peptide 3 is compared with the sequences which have been reported, in previous studies, to inhibit the binding with plasminogen or to bind to plasminogen, it can be seen that the YDLDFKT sequence, which is the latter portion of the sequence of the peptide 3, has a relatively high homology with the sequences of other species. Thus this sequence is thought to be a common plasminogen binding site. On the other hand, the NKT sequence, which is the first portion of the sequence of the peptide 3, is deleted in the sequences of other species. Thus, this sequence is thought to be a plasminogen binding site specific to *P. falciparum* (FIG. 14).

In general, the NKT sequence (present in the peptide 3) is a sequence to which an N-linked sugar chain binds, depending on the species. Thus, there arises a question that the confirmation of the presence or absence of glycosylation in the parasite enzyme may be necessary. However, the analysis results of SDS-PAGE (446 residues, 47 kD) and westernblotting proved the absence of glycosylation in *P. falciparum* enolase. In fact, it has been reported that N-linked and O-linked sugar chains were hardly found in *P. falciparum* or found in an extremely low level [Dieckmann-Schuppert A, Bender S, Odenthal-Schnittler M, Bause E, Schwarz R T. Apparent lack of N-glycosylation in the asexual intraerythrocytic stage of *Plasmodium falciparum*. Eur J Biochem. 1992, 205, 815-825. ; Gowda D C, Davidson E A. Reply. Parasitol Today. 2000, 16, 39-40.]. Accordingly, protein glycosylation observed in *P. falciparum* is GPI anchor glycosylation [Gowda D C, Davidson E A. Protein glycosylation in the malaria parasite. Parasitol Today. 1999, 15, 147-152. ; von Itzstein M, Plebanski M, Cooke B M, Coppel R L. Hot, sweet and sticky: the glycobiology of *Plasmodium falciparum*. Trends Parasitol, 2008, 24, 210-218.]. It is thought that enolase on the surface of a merozoite or an ookinete is presented by a GPI anchor mediated by the 432th Asn residue located in the vicinity of the C terminus of the protein.

Thus, the study of the present inventors led to an idea that the high anti-enolase antibody titer, which has been epidemiologically observed in the residents in malaria endemic areas, may be, for example, responsible for inhibiting the binding between enolase on the surface of the merozoite parasites and human plasminogen (and further, the invasion of ookinetes and merozoites into host cells).

Detailed descriptions are given below regarding the production methods of an antigen peptide (I') and an antigen peptide (II'), which are embodiments of the present invention, in Example 1. Detailed descriptions regarding the analysis data of the antigen peptide (I') and antigen peptide (II') are given in Example 2 and Example 3. Details regarding the preparation method of antigen-containing microparticles are given in Example 4, and details regarding the immunization with the antigen-containing microparticles are given in Example 5. However, the present invention is not limited by specific examples shown below, and alterations can of course be made. For example, a known biodegradable polymer other than those specified can be used as the polymer, and the amount and the concentration of the solution of the polymer can be adjusted as appropriate. Further, an antigen or microparticles other than those specified can be used in the antigen-containing microparticles, and the dose, and the amount and concentration of the solution can be adjusted as appropriate.

Example 1

Synthesis method for the antigen peptide (I') and the antigen peptide (II')

Synthesis schemes for synthesizing the antigen peptide (I') and the antigen peptide (II') are exemplified below ($E_5$-AD22-PG: SEQ ID NO: 6; $E_5$-AD22-PGC: SEQ ID NO: 7; K-E$_4$-C: SEQ ID NO: 8; and K-E$_4$-CK: SEQ ID NO: 9).
An example of production scheme of novel antigen peptide (I') (AD22map2-SS)
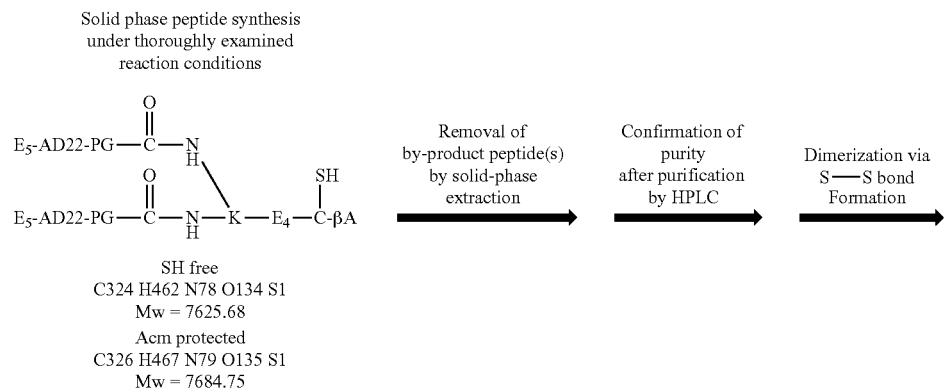
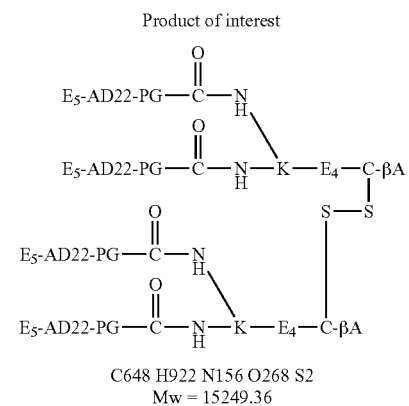
An example of production scheme of novel antigen peptide (II') o(AD22map2pal-SS)
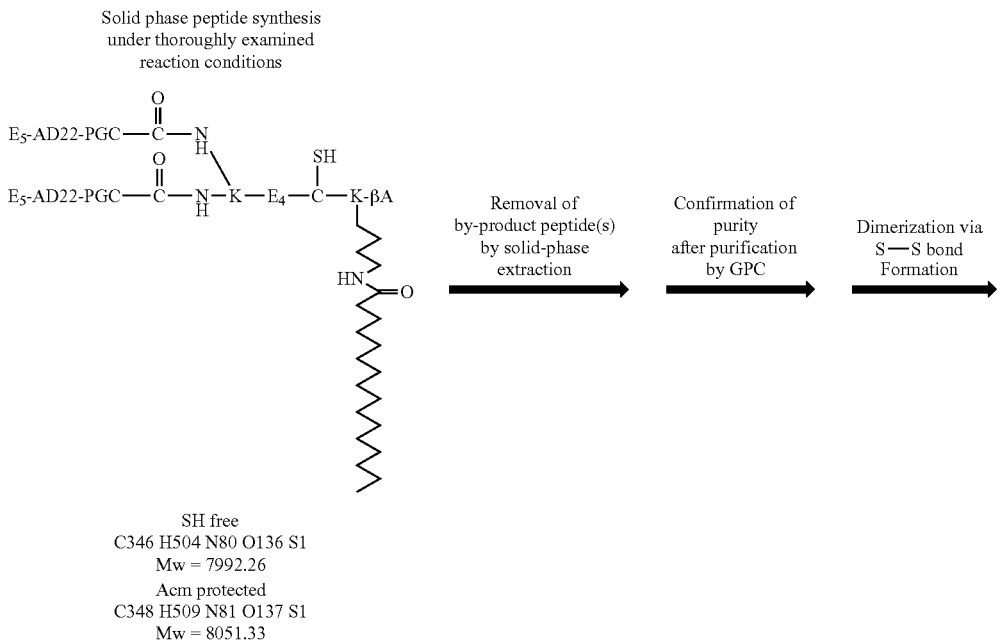

-continued

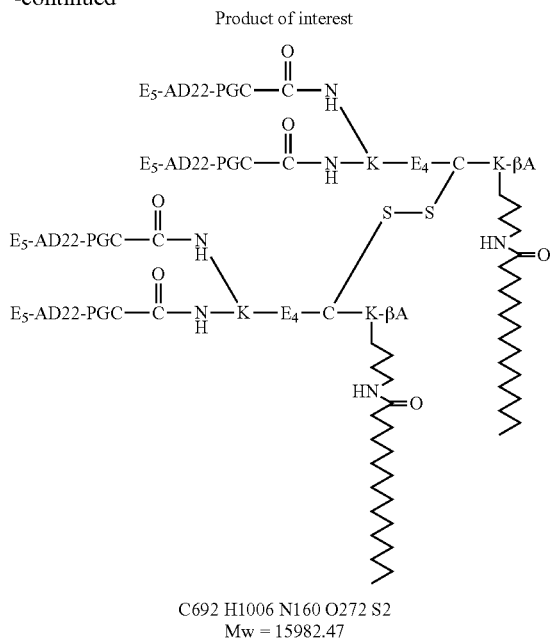

Product of interest

C692 H1006 N160 O272 S2
Mw = 15982.47

First, a monomer of each of the antigen peptide (I') and antigen peptide (II') (AD22map2 and AD22map2pal, respectively) was prepared by a common Fmoc peptide synthesis method. In the Fmoc peptide synthesis method, a Finoc-βAla-PEG resin (the amount of Fmoc amino acid introduced into the resin is defined herein as 1 eq), which is a resin into which the first amino acid is introduced in advance by an ordinary method, was used. For the deprotection of the Fmoc group, 2% DBU/DMF (or 30% piperidine/DMF) was used, and an Fmoc amino acid (10 eq), HCTU, HOBt (10 eq), and DIEA (20 eq) were used for condensation. The condensation was carried out for 30 min to extend the peptide chain.

After completing the extension to a full amino acid sequence, TFA: water: TIS: ethanedithiol=95:2.5:2.5:2.5 as a cleavage cocktail was added to the peptide-carrying resin, to cleave the peptide from the resin. Subsequently the filtrate was collected, and concentrated under reduced pressure. The resultant was then formed into a powder with diethyl ether, to obtain a crude product.

The identification of the crude product was carried out by HPLC and ESI-MS, followed by purification by solid-phase extraction, using Sep-Pak Vac 20 cc (5 g) (manufactured by Waters Corporation). Specifically, a 10% MeCNaq (0.1% TFA) solution of a sample was loaded onto a Sep-Pak column, and then solid-phase extraction was carried out, using a MeCN aqueous solution (0.1% TFA) as an elution solvent in an amount of 50 mL each at a gradient of from 20% to 30%.

After confirming the fraction of the product of interest by HPLC, the product of interest was obtained by freeze-drying. Subsequently, using a solution of the product of interest, formation of disulfide bonds by oxidation of iodine was carried out. The resulting solution was subjected to purification again, to finally obtain an antigen peptide.

Example 2

Analysis Data of Antigen Peptide (I') (AD22map2-SS)

Figure 3:
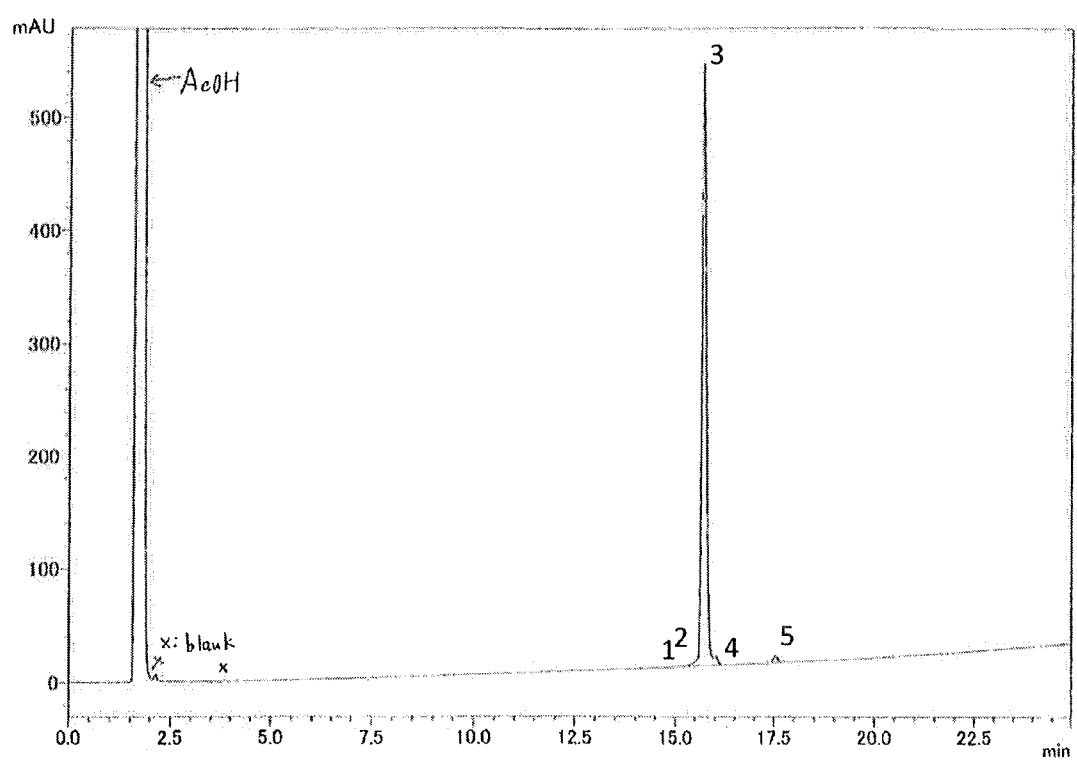
FIG. 3 shows an HPLC chromatogram of an antigen peptide (I') (AD22map2-SS).
Figure 4:
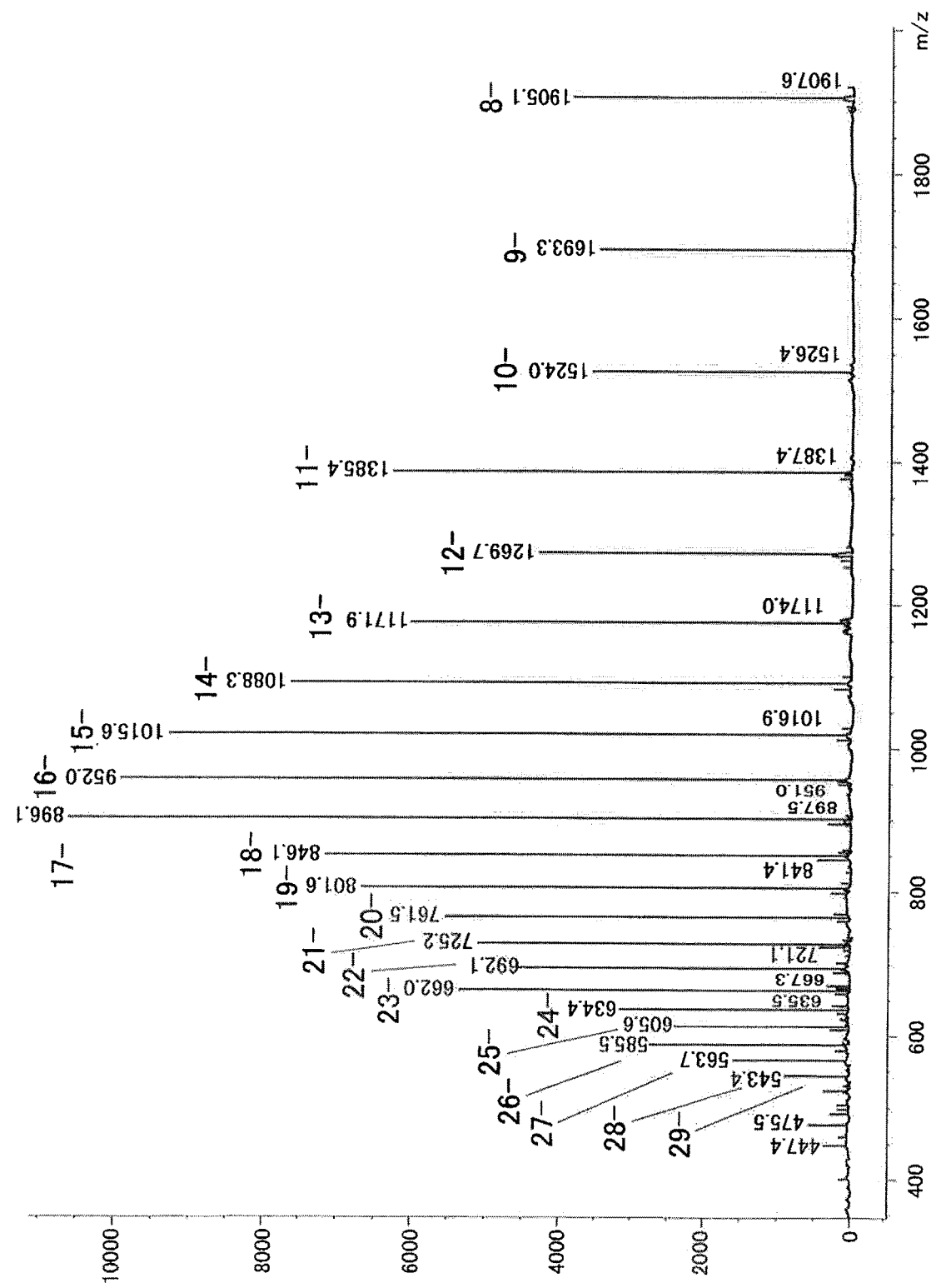
FIG. 4 shows ESI-MS data of the antigen peptide (I') (AD22map2-SS).

Appearance: white, freeze-dried product
Amino acid analysis values: (hydrolysis conditions: 6 M HCl aq. (with Phenol) 110° C., 22 hrs)
Asp (28) 28.00, Thr (8) 7.78, Ser (8) 7.21, Glu (36) 35. 62, Gly (4) 4.02, Ala (4) 4.00, Cys (2) 1.36, Leu (4) 4.03, Tyr (8) 8.00, Lys (10)10.07, NE13 (16) 18. 08, Pro (8) 8.18, Phe (8)+β-Ala (2) 10.01.
Purity (HPLC): 96.3% (FIG. 3)
Analysis conditions: Column, Zorbax 300SB-C18 (4.6×150 mm); Eluant: 10 to 60% MeCN/0,1% TFA (25 min); Temp.: 50° C.; Flow rate: 1.0 mlimin; Detector; 220 nm; Load: 4 µL (0.28 mg/0.560 mL 50% AcOH).
ESI-MS: MW=15249.3 (theoretical value: 15249.3) (FIG. 4)
Measurement condition
Apparatus: HP 1100 series LC/MSD, manufactured by Agilent Technologies
Sample concentration: 1 nmol/5 micro-L
Diluting solvent: 50% MeCN/H$_2$O:1 N NH$_3$ aq.=95:5

Example 3

Analysis Data of Antigen Peptide (II') (AD22map2pal-SS)

Figure 5:
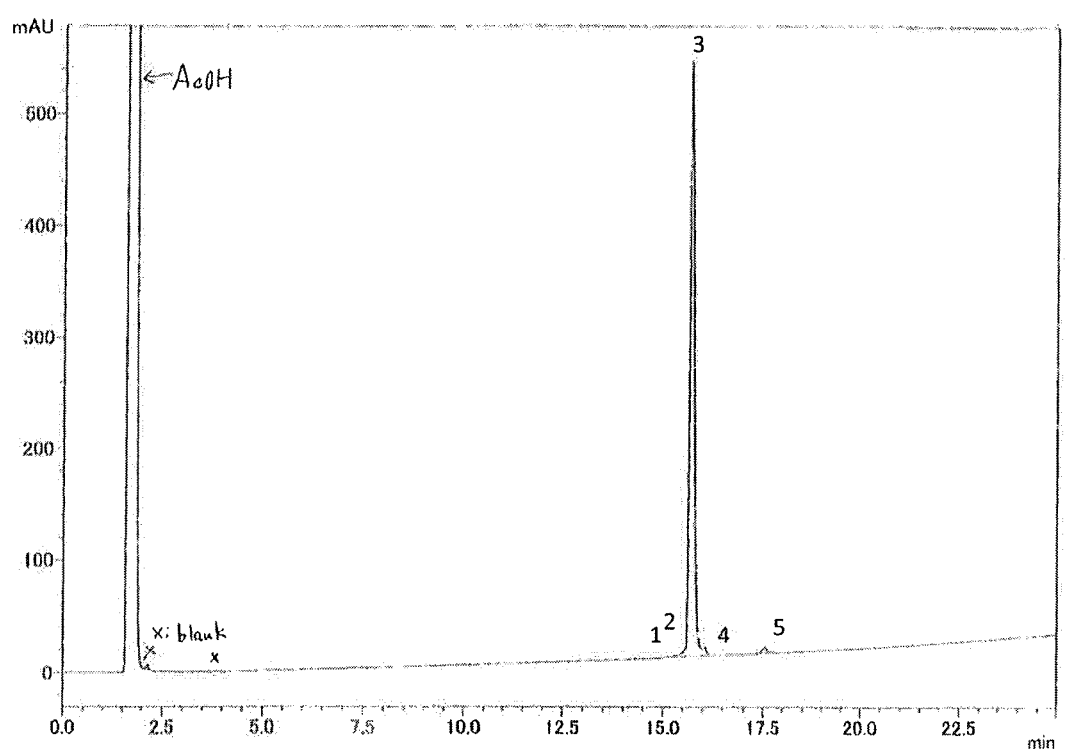
FIG. 5 shows an HPLC chromatogram of an antigen peptide (In (AD22map2pal-SS).
Figure 6:
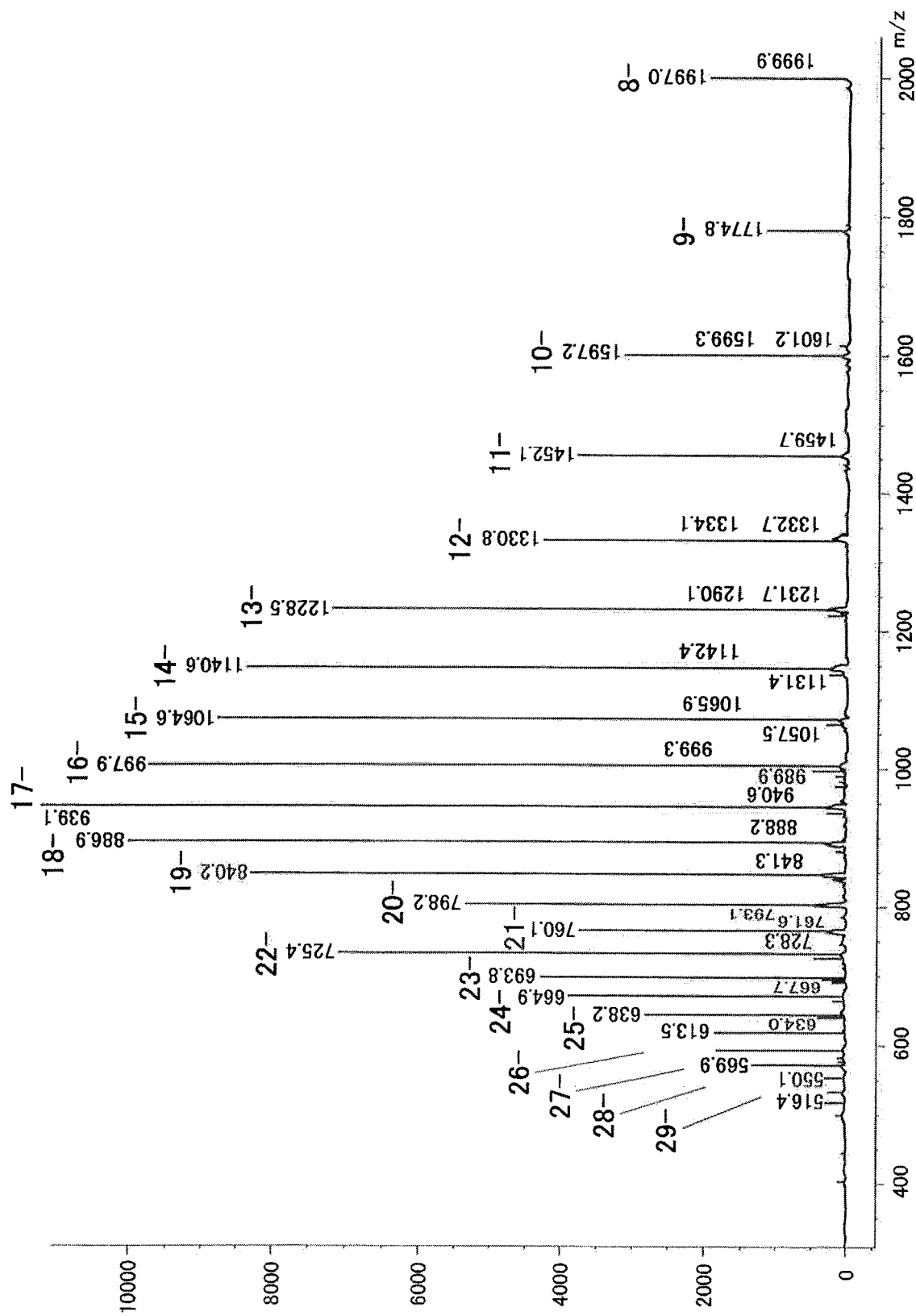
FIG. 6 shows ESI-MS data of the antigen peptide (II') (AD22map2pal-SS).

Appearance: white, freeze-dried product
Amino acid analysis values: (hydrolysis conditions: 6 M HCl aq. (with Phenol) 110° C., 22 hrs)
Asp (28) 27.96, Thr (8) 7.75, Ser (8) 7.21, Glu (36) 35.70, Gly (4) 4.01, Ala (4) 4.00, Cys (2) 1.90, Leu (4) 4.04, Tyr (8) 7.81, Lys (12) 11.99, NH3 (16) 17. 21, Pro (8) 8.20, Phe (8)+β-Ala (2) 9.98
Purity (HPLC): 96.4% (FIG. 5)
Analysis conditions: Column, Zorbax 300SB-C18 (4.6×150 mm); Eluant: 30-80% MeCN/0.1% TFA (25min); Temp.: 50° C.; Flow rate: 1.0 ml/min; Detector: 220 nm;
Load: 8 μL(0.32 mg/0.320 mL 50% AcOH).
ESI-MS: MW=15982.2 (theoretical value: 15982.5) (FIG. 6)
Measurement condition
Apparatus: HP 1100 series LC/MSD, manufactured by Agilent Technologies
Sample concentration: 1 nmol/5 micro-L
Diluting solvent: 50% MeCN/$H_2O$:1 N $NH_3$ aq.=95:5

Example 4

Preparation of Antigen-Containing Microparticles

Figure 7:
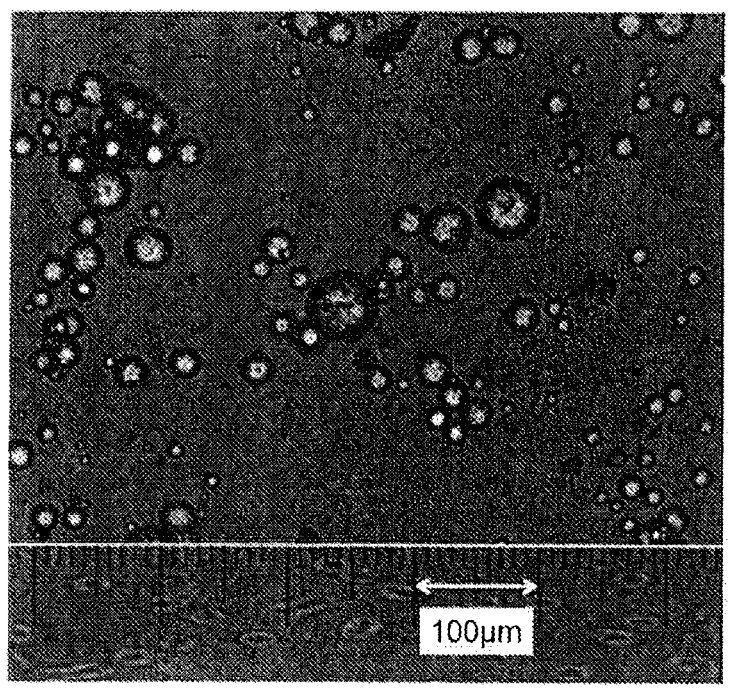
FIG. 7 is a light microscope photograph of antigen-containing microparticles used for immunization.

In this experiment, the antigen peptide (I') (AD22map2-SS) was used as the antigen, and antigen-containing microparticles were prepared by a method disclosed in JP 2009-256324 A. Specifically, the antigen-containing microparticles were prepared by a method including the steps of: mixing a solution containing an antigenic substance or a suspension containing an antigenic substance with a volatile organic solvent containing a biodegradable polymer; and further mixing the resulting mixed liquid with an aqueous solution of a negatively-charged polymer (FIG. 7). In the above described method, a poly(lactic acid-glycolic acid) copolymer (PLGA 7520, manufactured by Wako Pure Chemical Industries, Ltd.; composition ratio of lactic acid: glycolic acid 75:25) having an average molecular weight of 20,000 was used as the biodegradable polymer, and a 0.5% aqueous solution of polyvinyl alcohol was used as the aqueous solution of a negatively-charged polymer. The amount of antigen per unit weight of the microparticles was calculated from the CHN weight ratio obtained by elemental analysis, and determined to be 24 micro-g/mg.

Example 5

Immunization with Antigen-Containing Microparticles

In this Example, a detailed description will be given regarding the effect obtained in the case of immunizing Balb/c mice with the antigen-containing microparticles. Specifically, ten mice (female Balb/c mice) were immunized once, and blood was collected from each of the mice at week 3, week 6, and week 9 after the immunization, and the measurement of antibody titer in the serum of the collected blood was carried out.

Immunization experiment was carried out for the following two experimental groups (female Balb/c mice, five mice in each section). To each of the five mice in the group to be administered with the antigen, the antigen-containing microparticles prepared in Example 4 were administered subcutaneously in an amount of 10 μg in terms of the amount of antigen, thereby carrying out the immunization.
[Experimental group 1] To each of the mice, a suspension prepared by suspending the microparticles (0.41 mg) containing 10 μg of the antigen, in 200 μL of saline, was administered (immunized group).
[Experimental group 2] To each of the mice, 200 μL of an aqueous saline solution alone was administered (non-immunized group).

Figure 8:
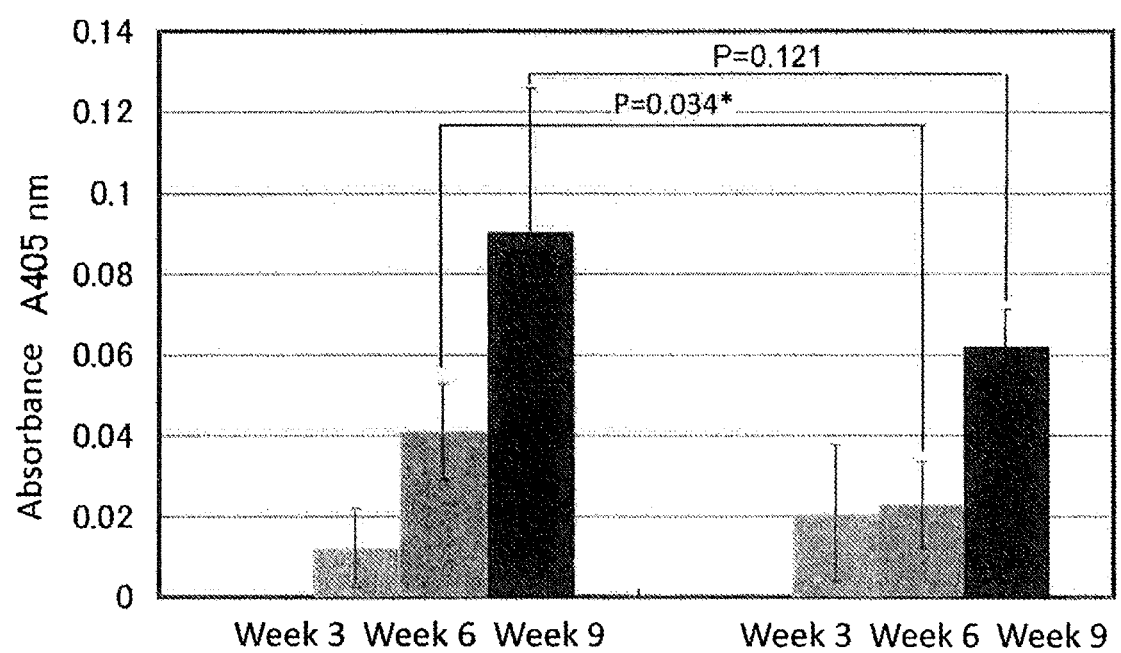
FIG. 8 is a graph showing the changes in IgG antibody titer against the peptide antigen, in the blood collected after immunization (at week 3, week 6, and week 9), in the immunized group (experimental group 1, left side in the figure) and the non-immunized group (experimental group 2, right side in the figure).
Figure 9:
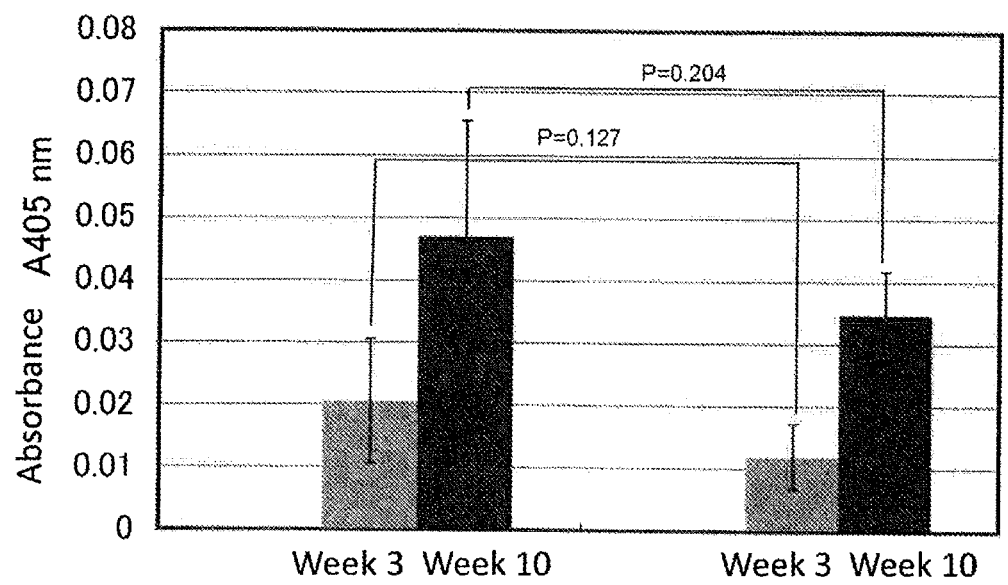
FIG. 9 is a graph showing the changes in IgG antibody titer against the peptide antigen, in the blood collected after immunization (at week 3, and week 10), in the immunized group (experimental group 1, left side in the figure) and the non-immunized group (experimental group 2, right side in the figure).

FIG. 8 and FIG. 9 show the changes in the IgG antibody titer against the antigen peptide (I') (AD22map2-SS) in the blood collected after the immunization (at week 3, week 6, week 9, and week 10), of the mice in the immunized group and the non-immunized group. The values of absorbance in ELISA at a dilution of 250-fold were plotted. The plot of absorbance is known to be approximately proportional to the plot of logarithm of the weight of the antibody.

The results shown in FIG. 8 and FIG. 9 revealed that, although immunization was carried out only once in the present Example, a statistically significant increase in the IgG antibody titer was observed in the mice in the immunized group, surprisingly, as compared to the non-immunized group. Therefore, in the present method, an increase in the IgG antibody titer against the peptide antigen was observed, in addition to a sustained increase in the antibody titer caused by the antigen-containing microparticles, and an immune effect due to parasite infection. The plot of absorbance is known to be approximately proportional to the plot of logarithm of the weight of the antibody.

Further, as an example of an additional experiment, it is possible to examine the effect of inhibiting parasite proliferation in vitro, for example, by adding the mouse antiserum obtained in Example 5 to a culture system of *P. falciparum*, at a dilution of 10-fold, 20-fold, and 200-fold. At this time, it is expected that an increased dilution ratio of the serum results in a decreased effect of inhibiting the rate of proliferation. This is a practically and generally used method, and it can be easily carried out in the present Example.

Still further, as an example of an additional experiment, it is possible to examine the effect of inhibiting parasite proliferation in vivo, or the effect of delaying or preventing the aggravation of symptoms or death in mice due to malaria infection, for example, by carrying out an infection experiment by abdominal administration of a lethal strain of a mouse malaria parasite (*Plasmodium berghei* ANKA, the number of parasites: $1\times10^6$) to the mice in Example 5. At this time, it is expected that an increased antibody titer results in a reduced rate of proliferation. This is a practically and generally used method, and it can be easily carried out in the present Example.

Based on the above described Examples regarding the production of the antigen peptide, the production of the antigen-containing microparticles, and the animal experiment utilizing immune reactions in mice, it has become possible to find out a method for delaying or preventing the aggravation of symptoms or death in humans due to malaria infection, by using the antigen peptide according to the present invention. In addition, based on the above Examples and the study results of the present inventors, it has become possible to device a method for applying bioactive peptide for inducing an immune reaction in a human, which method allows for induction of an immune response against malaria parasites in humans, which has been hitherto impossible.

INDUSTRIAL APPLICABILITY

The present invention can be used in pharmaceuticals, reagents and the like.

The invention claimed is:

1. A peptide comprising a structure in which two peptides each consisting of (i) an amino acid sequence represented by: A01-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-A02 (SEQ ID NO: 1) or (ii) an amino acid sequence represented by: A03-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Lys-Ser-Leu-Val-Lys-Thr-A04 (SEQ ID NO: 2) are linked by amide bonds between the respective carboxy termini of the two peptides and two amino groups of Lys in a linker peptide represented by the following (iii):

(iii) Lys-A05-Cys-A06 and arranged in the form of a two-forked branch, wherein in the above (i), (ii), and (iii), A01 to A06 each represent 0 or an arbitrary number of amino acid residues.

2. The peptide according to claim 1, which is represented by the following (I) or (II):

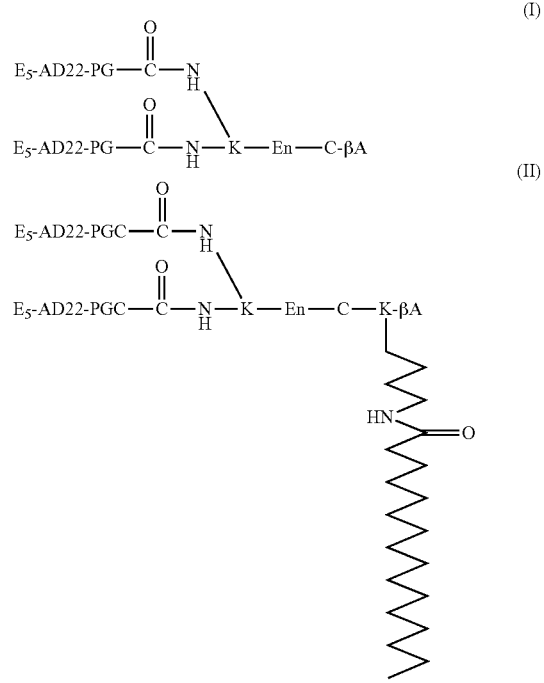

wherein AD22 represents the amino acid sequence of SEQ ID NO: 1; and n represents an integer of 4 or 5.

3. A peptide comprising a dimerized structure in which two peptides each according to claim 1 are linked by an S—S bond between the Cys residues in the linker peptide sequences, each represented by the above (iii), included in the respective two peptides.

4. The peptide according to claim 3, which is represented by the following (I') or (II'):

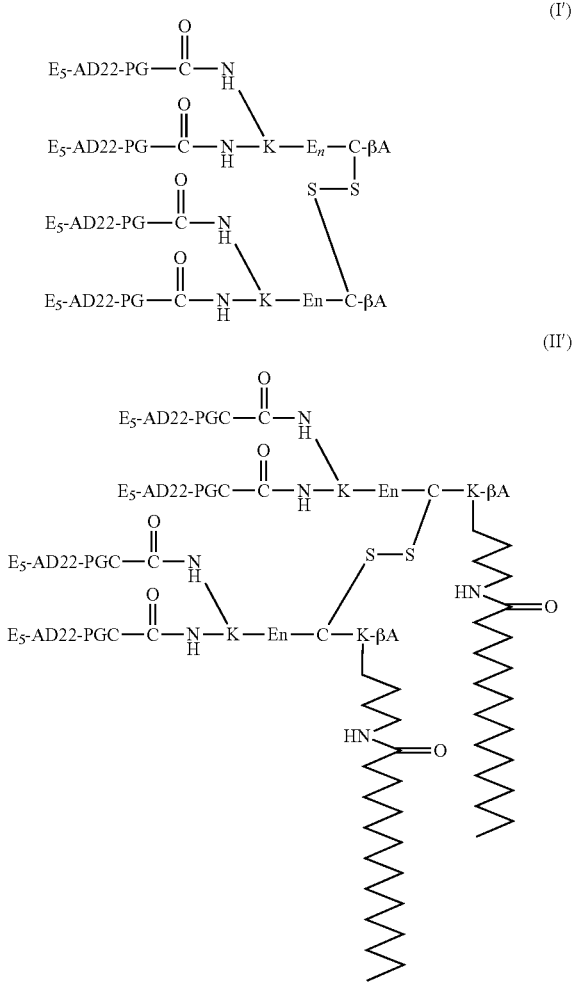

wherein AD22 represents the amino acid sequence of SEQ ID NO: 1; and n represents an integer of 4 or 5.

5. Microparticles comprising the peptide according to claim 1 produced by the steps of:

mixing a solution of the peptide according to claim 1 with a volatile organic solvent comprising a biodegradable polymer to prepare an emulsion; and mixing the resulting emulsion with an aqueous solution of a negatively-charged polymer.

6. The microparticles comprising said peptide according to claim 5, wherein the biodegradable polymer is a polylactic acid-glycolic acid copolymer.

7. The microparticles comprising said peptide according to claim 5, wherein the biodegradable polymer is a polydepsipeptide.

8. A pharmaceutical composition for preventing or treating a malaria parasite infection, wherein the composition comprises microparticles comprising said peptide according to claim 5, and a pharmaceutically acceptable carrier.

9. A substance comprising the peptide according to claim 1 and a film, latex particles, ultrafine metal particles, or a plastic plate, wherein the peptide is bound to a solid phase surface of the film, the latex particles, the ultrafine metal particles, or the plastic plate.

10. A test method for measuring malaria antibody titer in serum or plasma, the method comprising the step of measuring malaria antibody titer in serum or plasma, using the substance according to claim 9.

11. A method for measuring the antibody titer of an individual administered the peptide according to claim 1, the method comprising the step of measuring an antibody against the peptide according to claim 1, using the substance obtained by allowing the peptide according to claim 1 to bind to a solid phase surface of a film, latex particles, ultrafine metal particles or a plastic plate.

* * * * *